(12) United States Patent
Arnett

(10) Patent No.: US 10,024,355 B2
(45) Date of Patent: **\*Jul. 17, 2018**

(54) POLYAXIAL LOCKING INTERFACE

(71) Applicant: IMDS LLC, Providence, UT (US)

(72) Inventor: Jeffery D. Arnett, Gilbert, AZ (US)

(73) Assignee: IMDS LLC, Providence, UT (US)

( * ) Notice: Subject to any disclaimer, the term of this patent is extended or adjusted under 35 U.S.C. 154(b) by 90 days.

This patent is subject to a terminal disclaimer.

(21) Appl. No.: 15/221,364

(22) Filed: Jul. 27, 2016

(65) Prior Publication Data

US 2016/0333920 A1    Nov. 17, 2016

Related U.S. Application Data

(63) Continuation of application No. 14/075,700, filed on Nov. 8, 2013, now Pat. No. 9,404,525, which is a continuation-in-part of application No. 13/828,584, filed on Mar. 14, 2013, now Pat. No. 9,103,367.

(51) Int. Cl.
| | |
|---|---|
| *F16B 39/00* | (2006.01) |
| *F16B 39/28* | (2006.01) |
| *A61B 17/80* | (2006.01) |
| *A61B 17/86* | (2006.01) |

(52) U.S. Cl.
CPC .......... *F16B 39/28* (2013.01); *A61B 17/8052* (2013.01); *A61B 17/8057* (2013.01); *A61B 17/86* (2013.01); *F16B 39/00* (2013.01); *A61B 2017/8655* (2013.01)

(58) Field of Classification Search
CPC .......... F16B 23/00; F16B 35/06; F16B 39/00; F16B 39/28; F16B 39/282

USPC .......................................... 411/166, 402, 403
See application file for complete search history.

(56) References Cited

U.S. PATENT DOCUMENTS

| | | | |
|---|---|---|---|
| 2,400,318 | A | 5/1946 | Rosan |
| 2,588,372 | A | 3/1952 | Erb |
| 3,408,887 | A | 11/1968 | Villo |
| 5,012,706 | A | 5/1991 | Wright |
| 5,358,367 | A | 10/1994 | Yang |
| 5,375,956 | A | 12/1994 | Pennig |
| 5,558,674 | A | 9/1996 | Heggeness |
| 5,904,683 | A | 5/1999 | Pohndorf |
| 5,954,722 | A | 9/1999 | Bono |
| 6,258,089 | B1 | 7/2001 | Campbell |
| 6,296,642 | B1 | 10/2001 | Morrison |
| 6,306,140 | B1 | 10/2001 | Siddiqui |

(Continued)

FOREIGN PATENT DOCUMENTS

| | | |
|---|---|---|
| DE | 4343117 | 11/1999 |
| EP | 1712197 | 1/2009 |

(Continued)

*Primary Examiner* — Roberta S Delisle
(74) *Attorney, Agent, or Firm* — Maywood IP Law; G. Jo Hays; David W. Meibos

(57) ABSTRACT

An interlocking interface retains a screw head in a socket to prevent migration of the screw head out of the socket, or to lock the screw head in the socket. The interlocking interface may retain or lock the screw at various polyaxial angles with respect to the socket. The screw head includes external corrugations. The socket includes an internal corrugated structure which interlocks with the external corrugations of the screw head when the screw is at various polyaxial angles with respect to the socket. A counterbore may be adjacent either or both ends of the socket.

17 Claims, 41 Drawing Sheets

(56) References Cited

U.S. PATENT DOCUMENTS

| | | |
|---|---|---|
| 6,322,562 B1 | 11/2001 | Wolter |
| 6,719,759 B2 | 4/2004 | Wagner |
| 6,730,091 B1 | 5/2004 | Pfefferle |
| 6,955,677 B2 | 10/2005 | Dahners |
| 6,974,461 B1 | 12/2005 | Wolter |
| 6,976,816 B2 | 12/2005 | Slesinski |
| 6,997,660 B2 | 2/2006 | Fedor |
| 7,137,987 B2 | 11/2006 | Patterson |
| 7,179,260 B2 | 2/2007 | Gerlach |
| 7,220,263 B2 | 5/2007 | Cordaro |
| 7,682,379 B2 | 3/2010 | Mathieu |
| 7,794,482 B2 | 9/2010 | Mathieu |
| 7,905,909 B2 | 3/2011 | Orbay |
| 7,922,433 B2 | 4/2011 | Ricciardo |
| 7,955,364 B2 | 6/2011 | Ziolo |
| 8,246,661 B2 | 8/2012 | Beutter |
| 8,337,535 B2 | 12/2012 | White |
| 8,343,196 B2 | 1/2013 | Schneider |
| 8,398,682 B2 | 3/2013 | Jackson |
| 8,496,694 B2 | 7/2013 | Hashmi |
| 8,506,607 B2 | 8/2013 | Eckhof |
| 8,574,268 B2 | 11/2013 | Chan |
| 9,103,367 B2 | 8/2015 | Arnett |
| 9,404,525 B2 | 8/2016 | Arnett |
| 2007/0043366 A1 | 2/2007 | Pfefferle |
| 2008/0140130 A1 | 6/2008 | Chan |
| 2008/0208259 A1 | 8/2008 | Gilbert |
| 2008/0234749 A1 | 9/2008 | Forstein |
| 2009/0088807 A1 | 4/2009 | Castaneda |
| 2010/0312286 A1 | 12/2010 | Dell'Oca |
| 2011/0295325 A1 | 12/2011 | Wagner |
| 2011/0301608 A1 | 12/2011 | Roth |
| 2012/0259371 A1 | 10/2012 | Mathieu |
| 2012/0323284 A1 | 12/2012 | Baker |
| 2014/0271028 A1 | 9/2014 | Arnett |
| 2014/0271029 A1 | 9/2014 | Arnett |
| 2014/0277180 A1 | 9/2014 | Paolino |
| 2014/0358230 A1 | 12/2014 | Niese |

FOREIGN PATENT DOCUMENTS

| | | |
|---|---|---|
| EP | 2529685 | 4/2014 |
| EP | 2967690 | 1/2016 |
| JP | 2011067642 | 4/2011 |
| WO | WO2000053110 | 9/2000 |
| WO | WO2009023666 | 2/2009 |
| WO | WO2014168714 | 10/2014 |

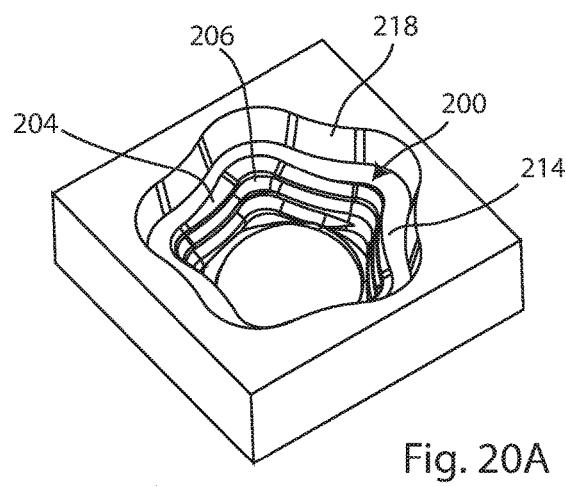
Fig. 20A
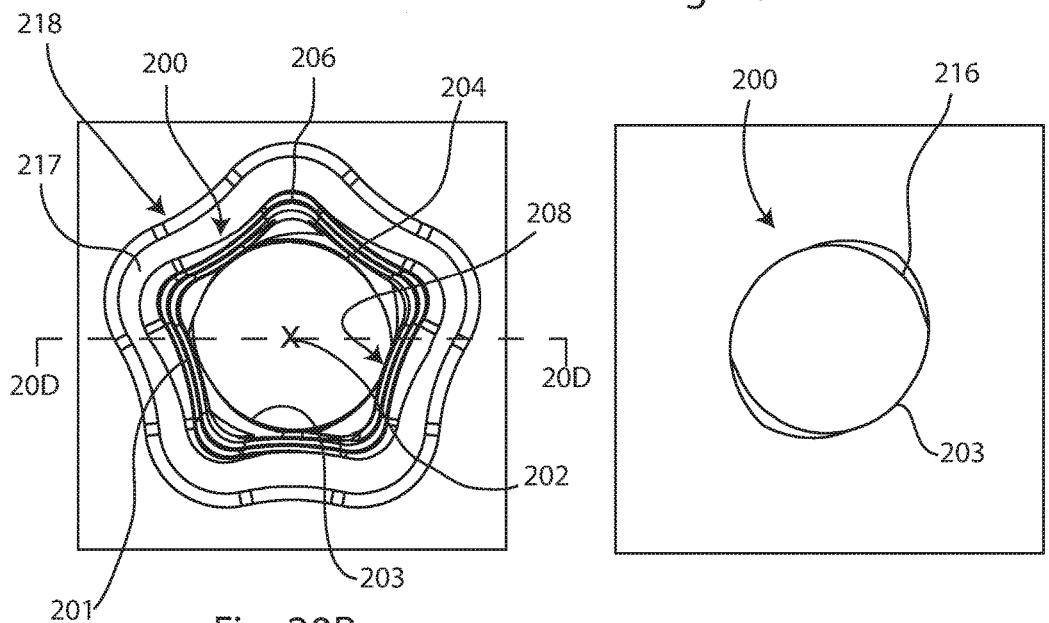
Fig. 20B
Fig. 20C

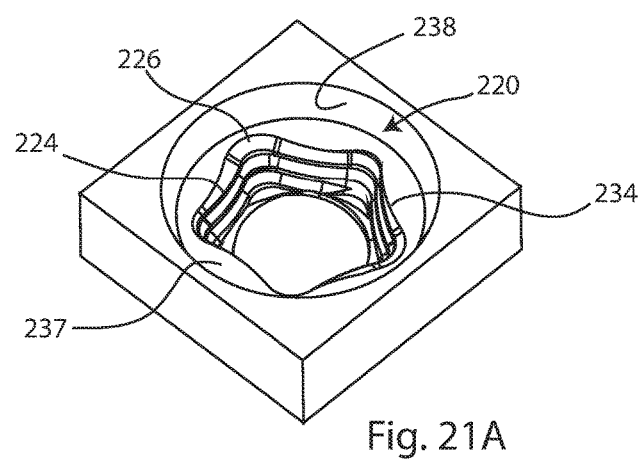
Fig. 21A
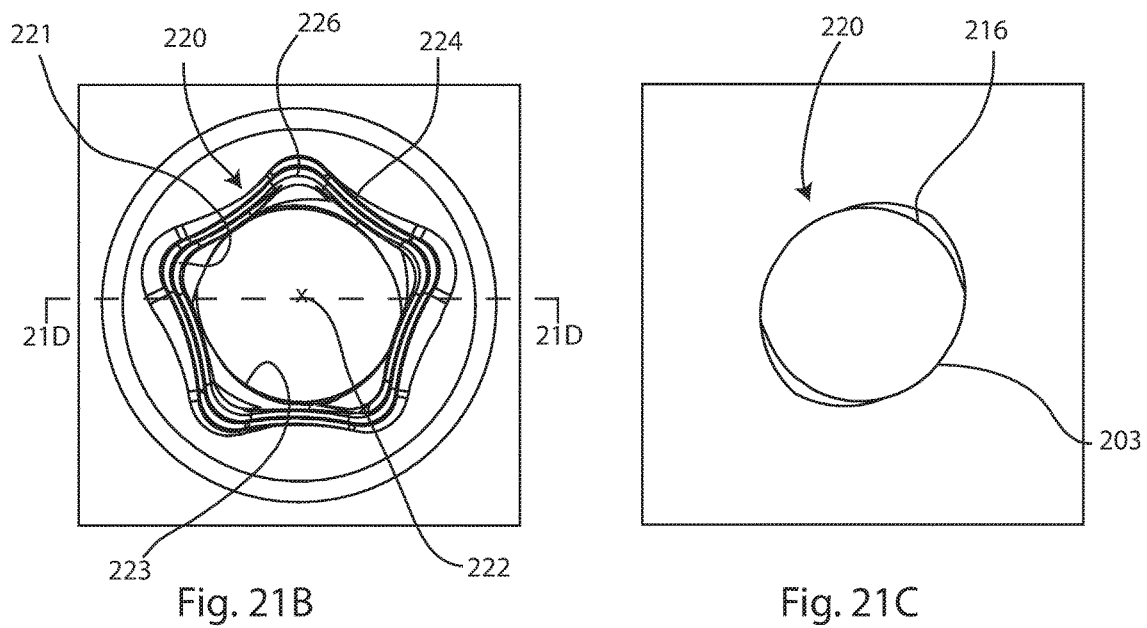
Fig. 21B
Fig. 21C

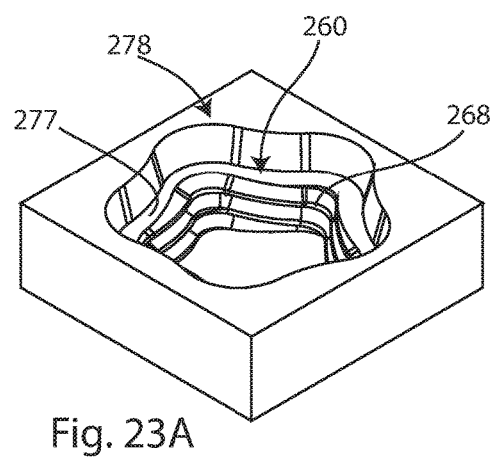
Fig. 23A
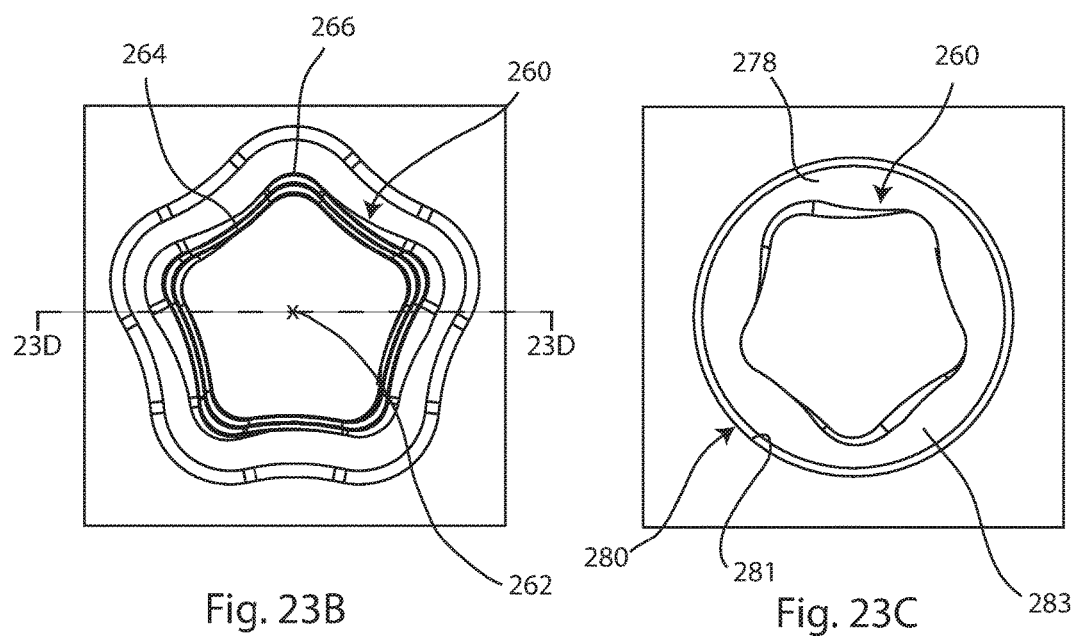
Fig. 23B
Fig. 23C

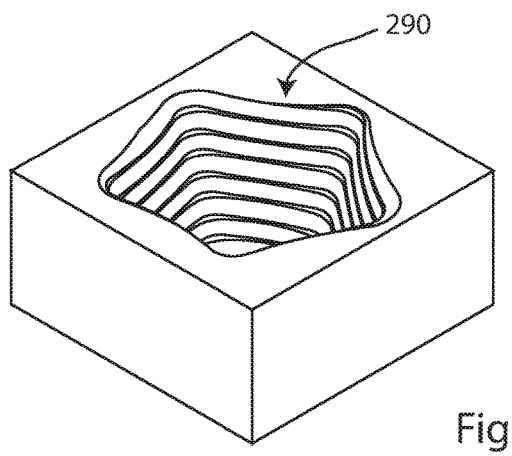
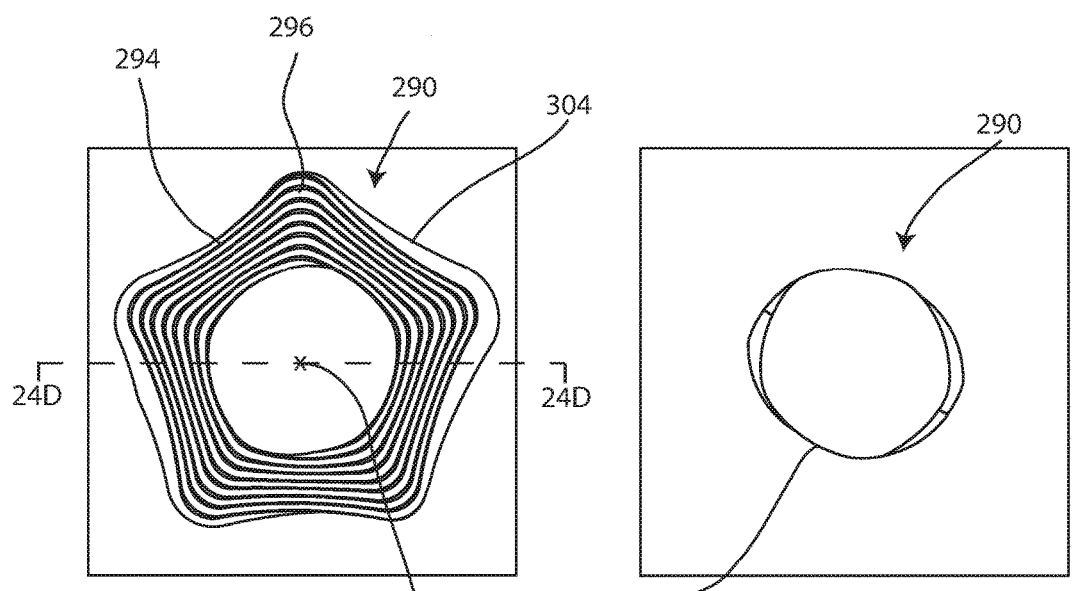
Fig. 24A
Fig. 24B
Fig. 24C

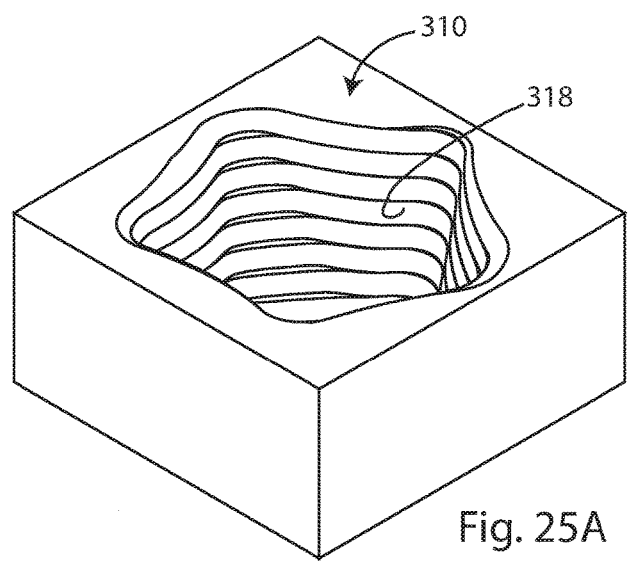
Fig. 25A
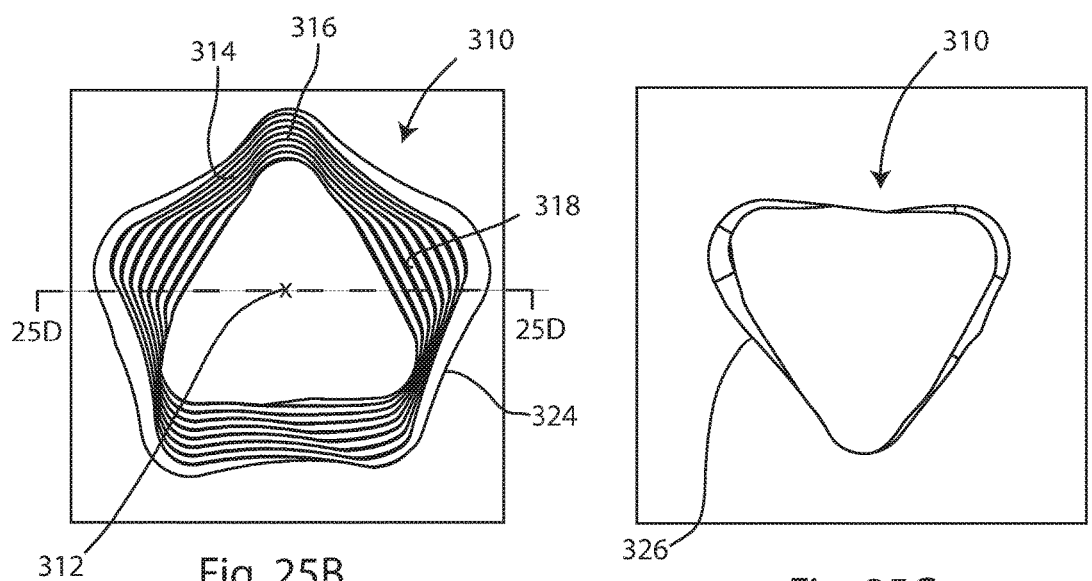
Fig. 25B
Fig. 25C

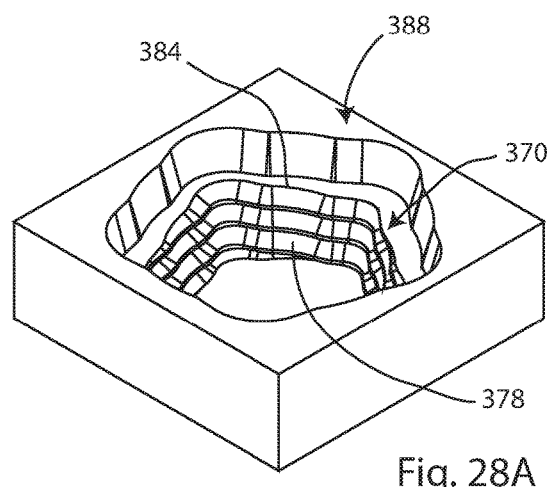
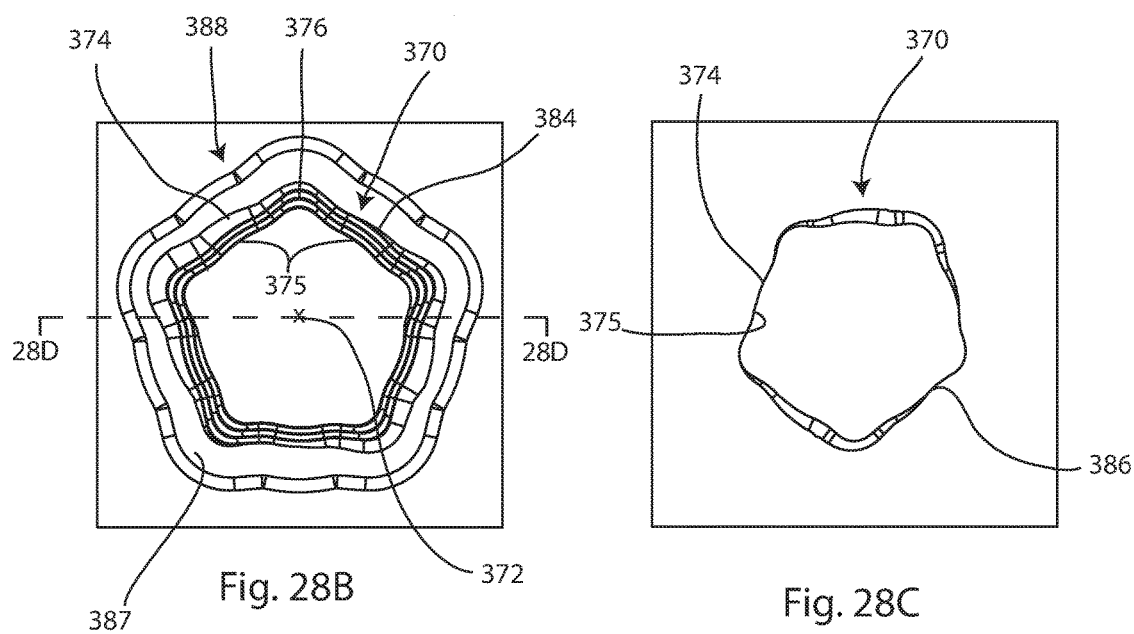

POLYAXIAL LOCKING INTERFACE

CROSS-REFERENCE TO RELATED APPLICATIONS

The present application is a continuation of:

U.S. patent application Ser. No. 14/075,700, filed Nov. 8, 2013, entitled POLYAXIAL LOCKING INTERFACE, which is pending.

U.S. patent application Ser. No. 14/075,700 is a continuation-in-part of:

U.S. patent application Ser. No. 13/828,584, filed Mar. 14, 2013, entitled POLYAXIAL LOCKING INTERFACE, which issued Aug. 11, 2015 as U.S. Pat. No. 9,103,367.

The above referenced documents are incorporated herein by reference in their entirety.

BACKGROUND

The present disclosure relates to retention interfaces in medical devices, such as to prevent a screw from migrating, unthreading, "backing out" and the like. This disclosure also relates to interlocking interfaces, such as screw head and device holes, such as bone plate holes. The principles herein are applicable wherever it is desired to prevent a part from migrating relative to a corresponding socket and/or wherever it is desired to lock a part to a socket.

BRIEF DESCRIPTION OF THE DRAWINGS

While examples of the present technology have been shown and described in detail below, it will be clear to the person skilled in the art that variations, changes and modifications may be made without departing from its scope. As such, that which is set forth in the following description and accompanying drawings is offered by way of illustration only and not as a limitation. The actual scope of the invention is intended to be defined by the following claims, along with the full range of equivalents to which such claims are entitled.

In the following Detailed Description, various features are grouped together in several examples for the purpose of streamlining the disclosure. This method of disclosure is not to be interpreted as reflecting an intention that examples of the technology require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

Figure 1:
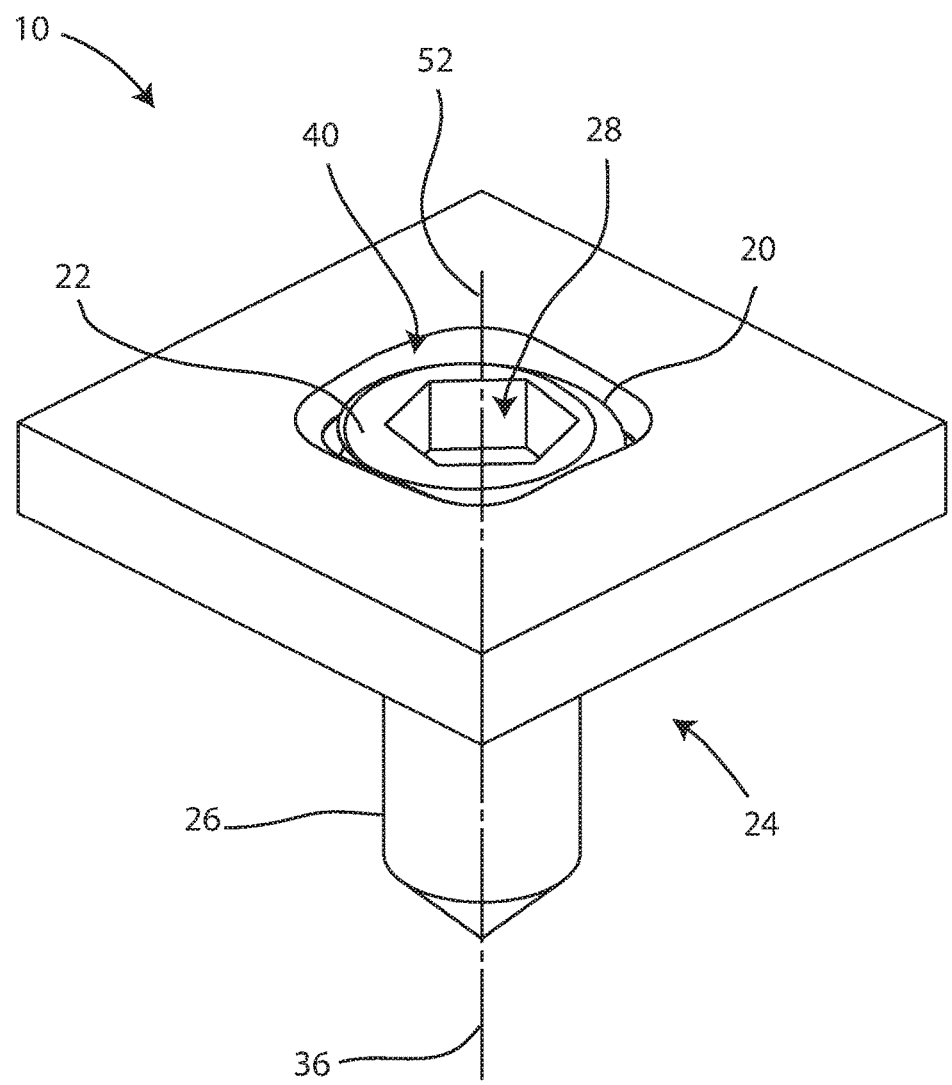

Identical reference numerals do not necessarily indicate an identical structure. Rather, the same reference numeral may be used to indicate a similar feature or a feature with similar functionality. Not every feature of each example is labeled in every figure in which that example appears, in order to keep the figures clear. Similar reference numbers (e.g., those that are identical except for the first numeral) are used to indicate similar features in different examples.

Figure 2:
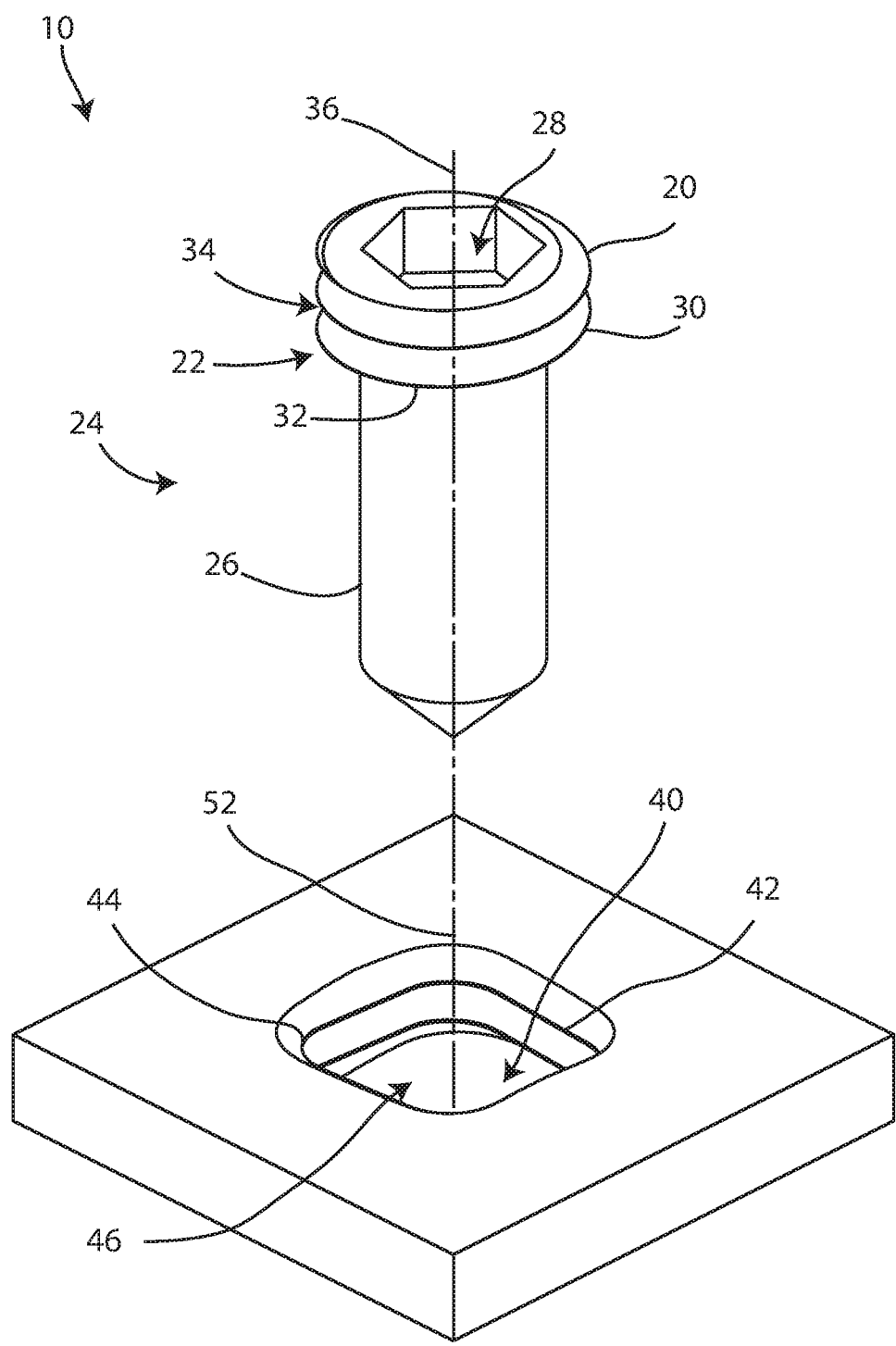
Figure 3:
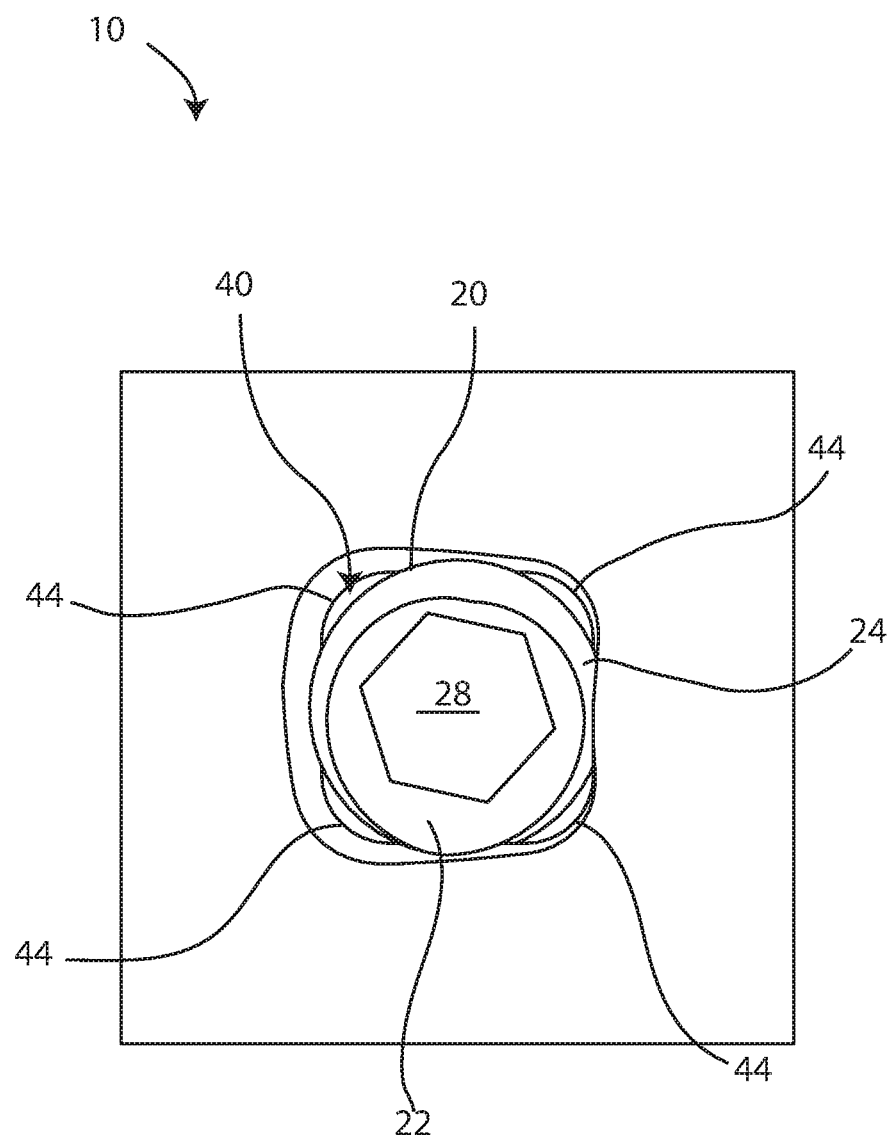
Figure 4A:
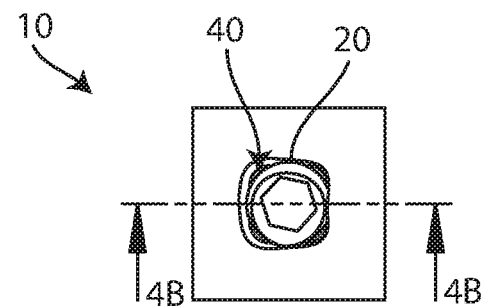
Figure 4B:
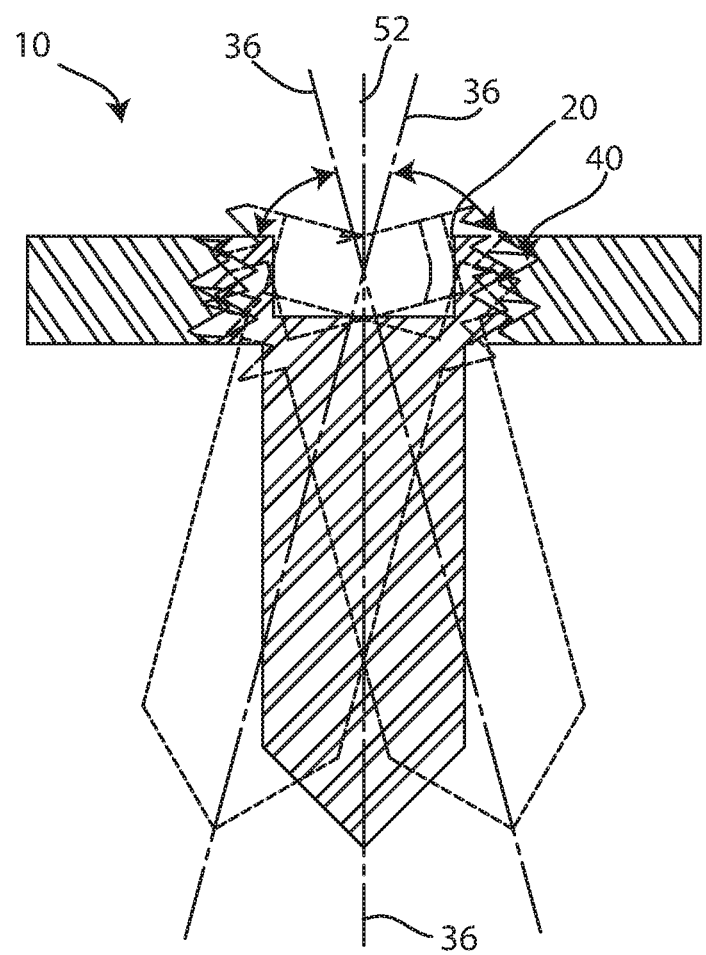
Figure 4C:
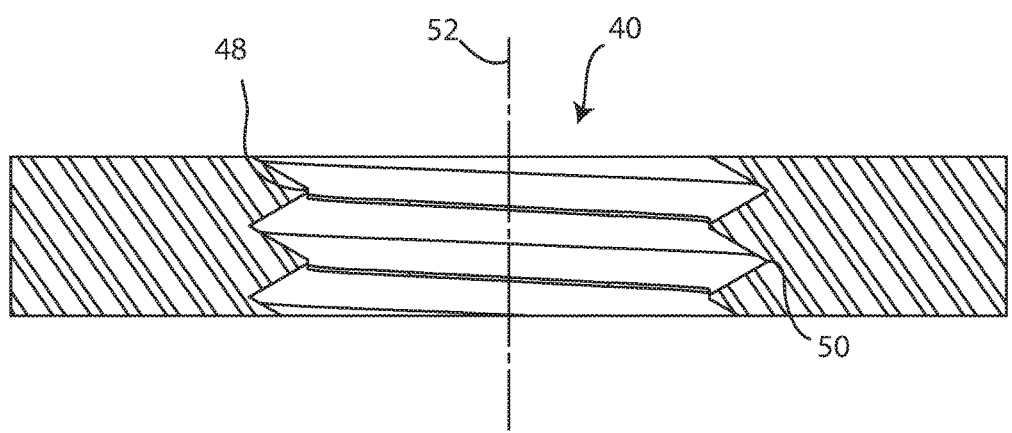
Figure 5:
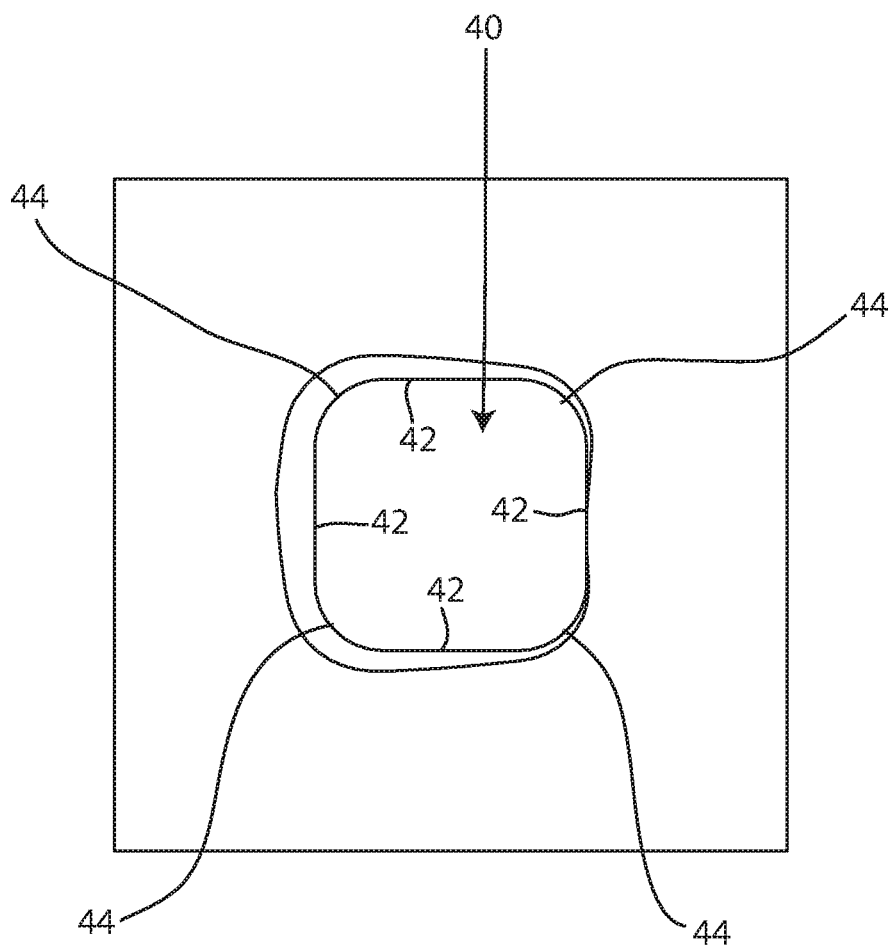
Figure 6:
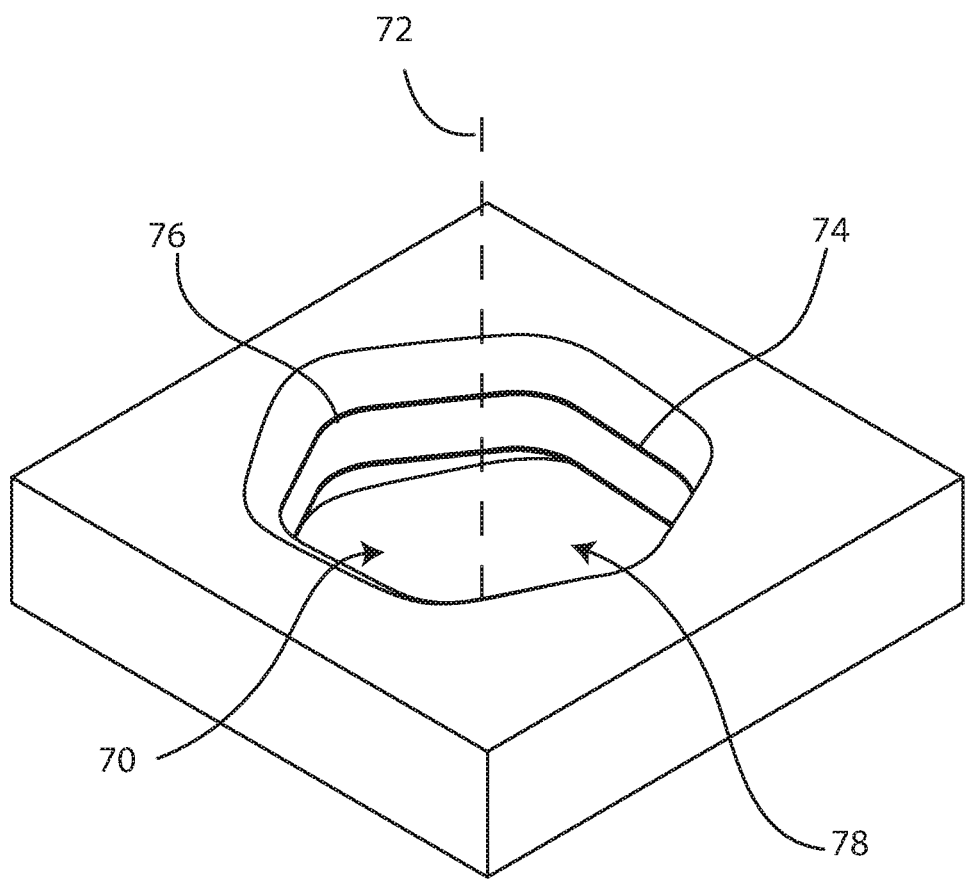
Figure 7A:
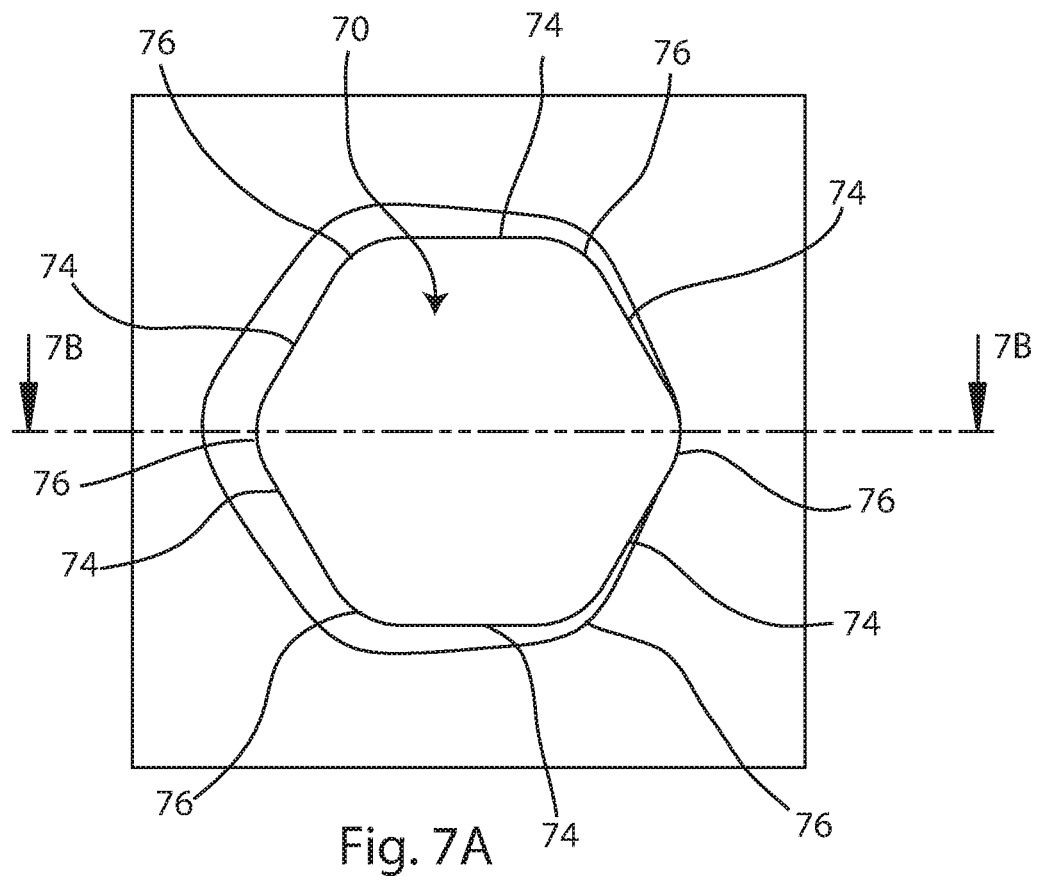
Figure 7B:
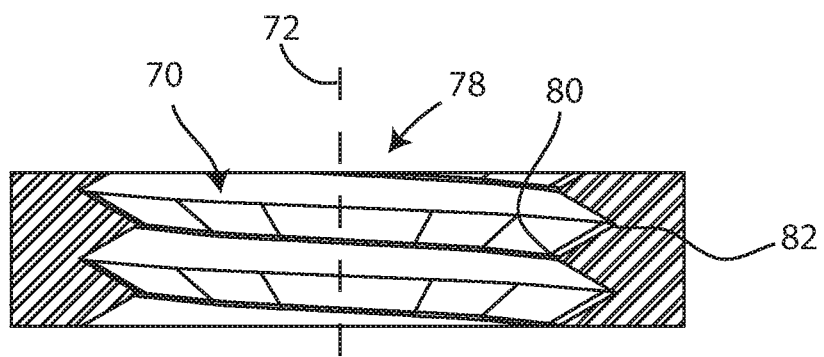
Figure 8:
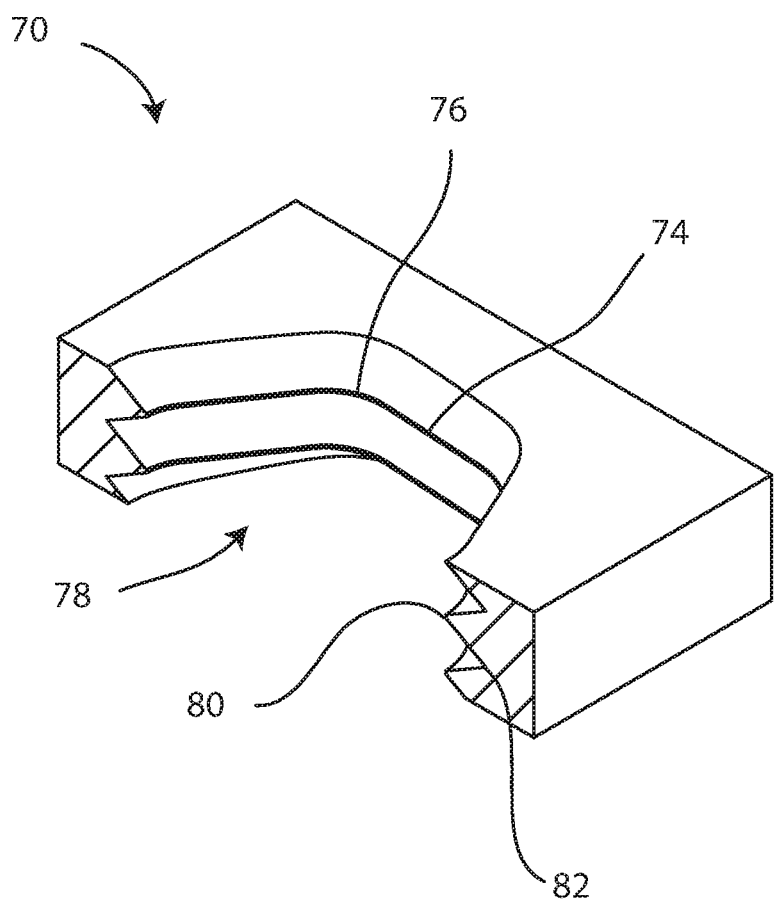
Figure 9:
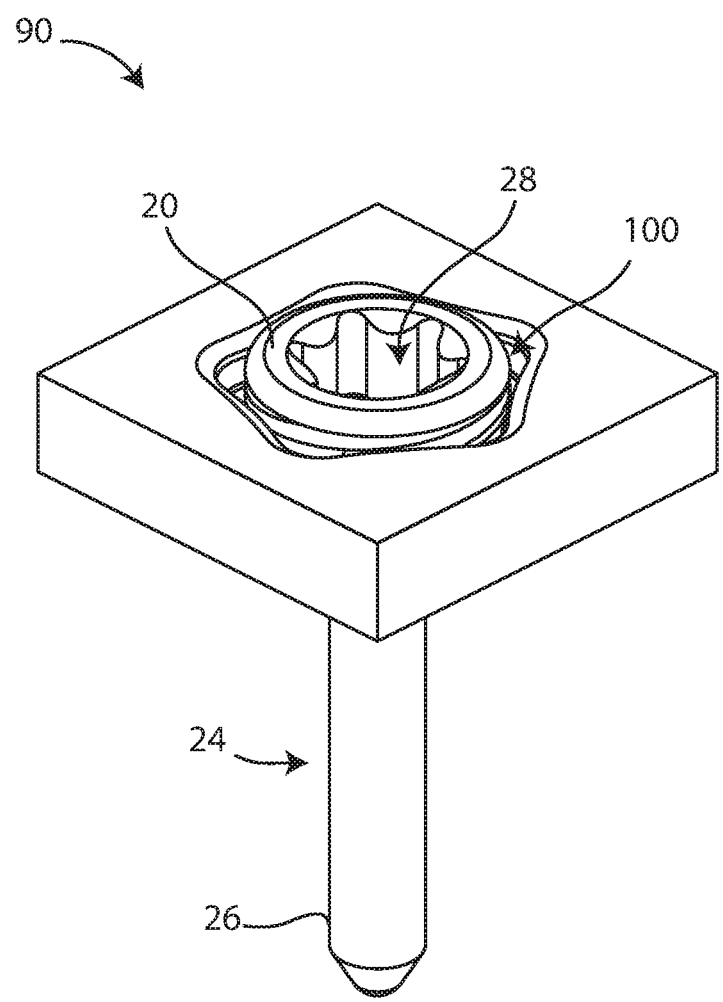
Figure 10:
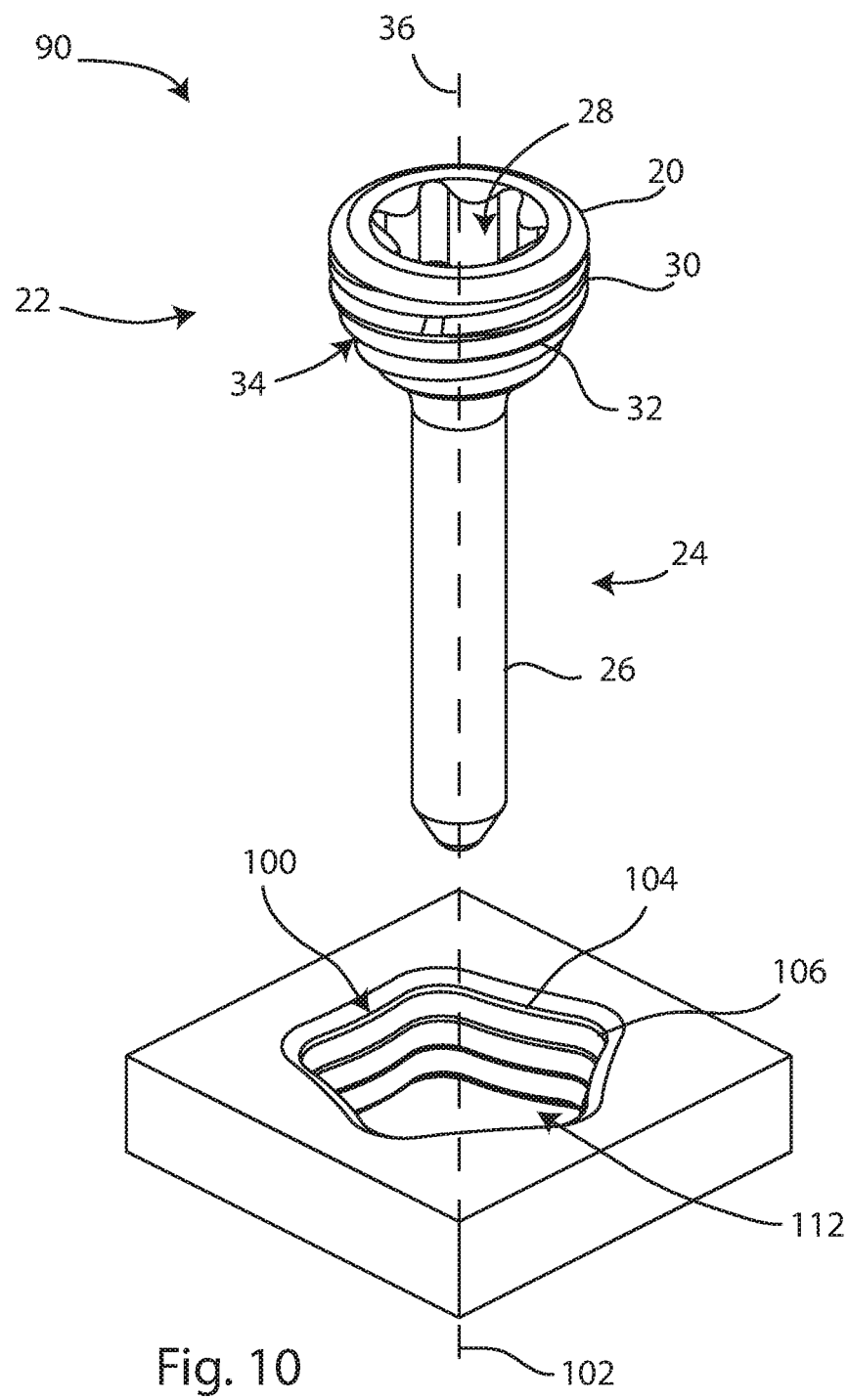
Figure 11A:
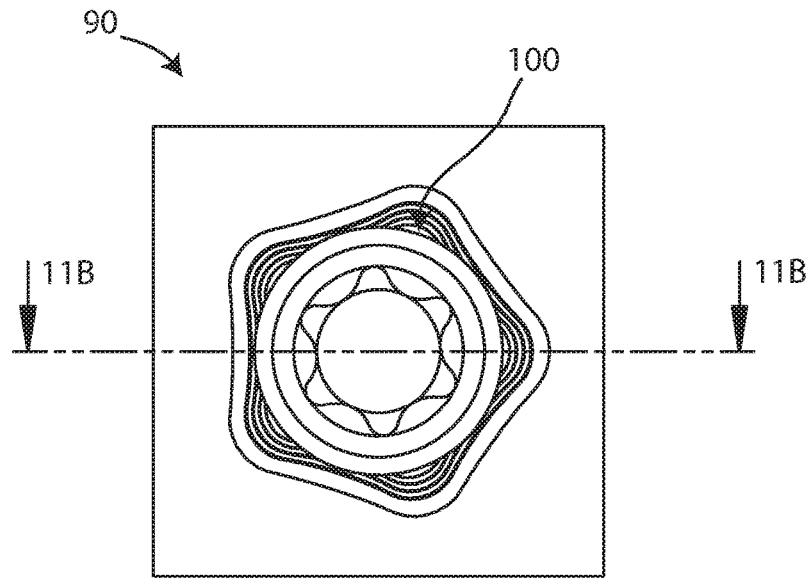
Figure 11B:
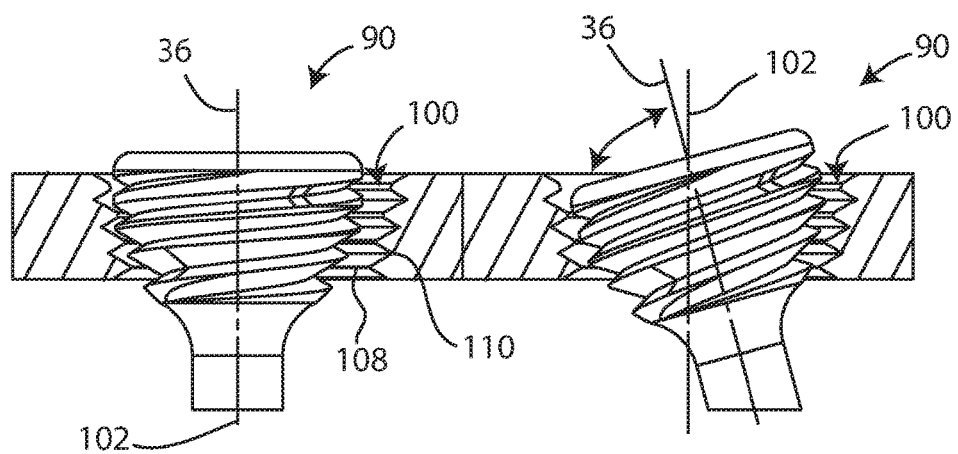
Figure 12:
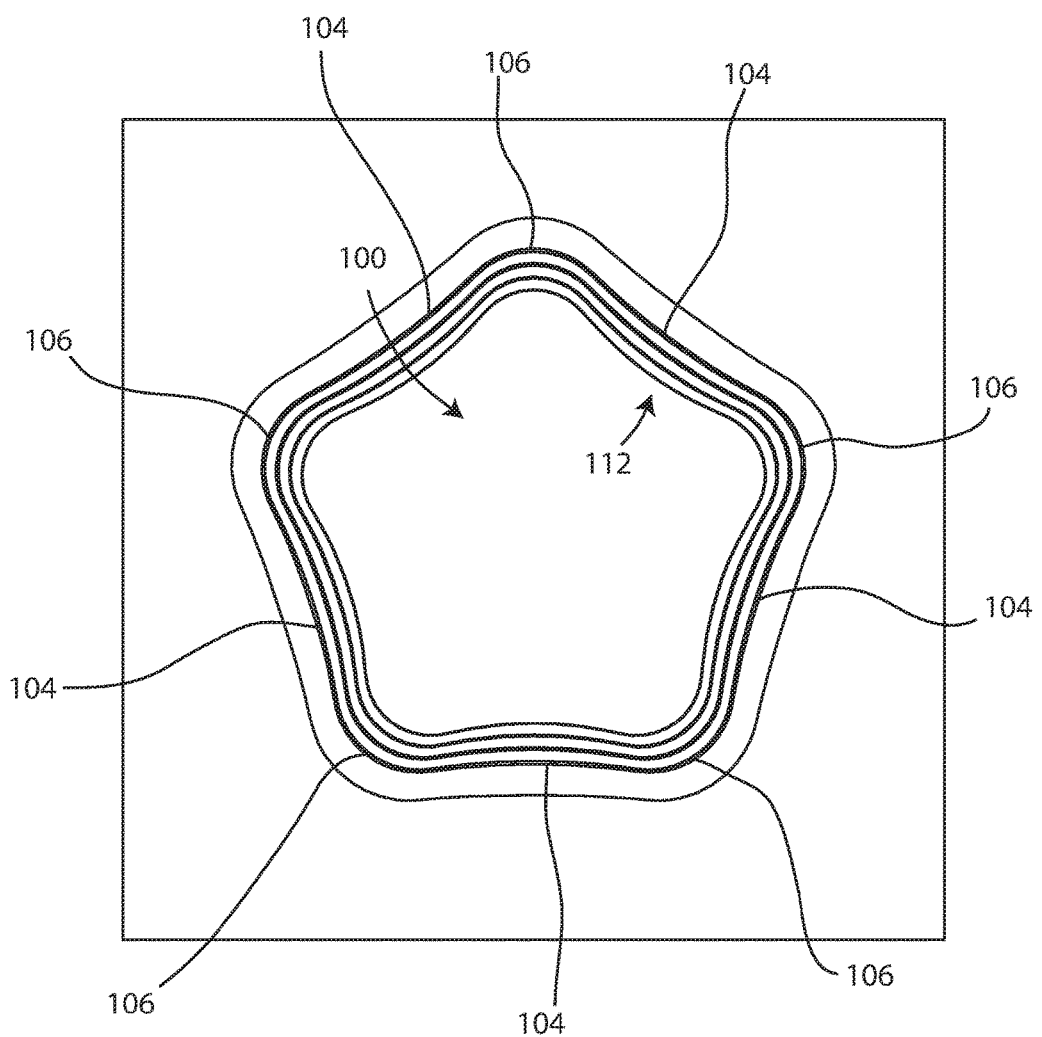
Figure 13:
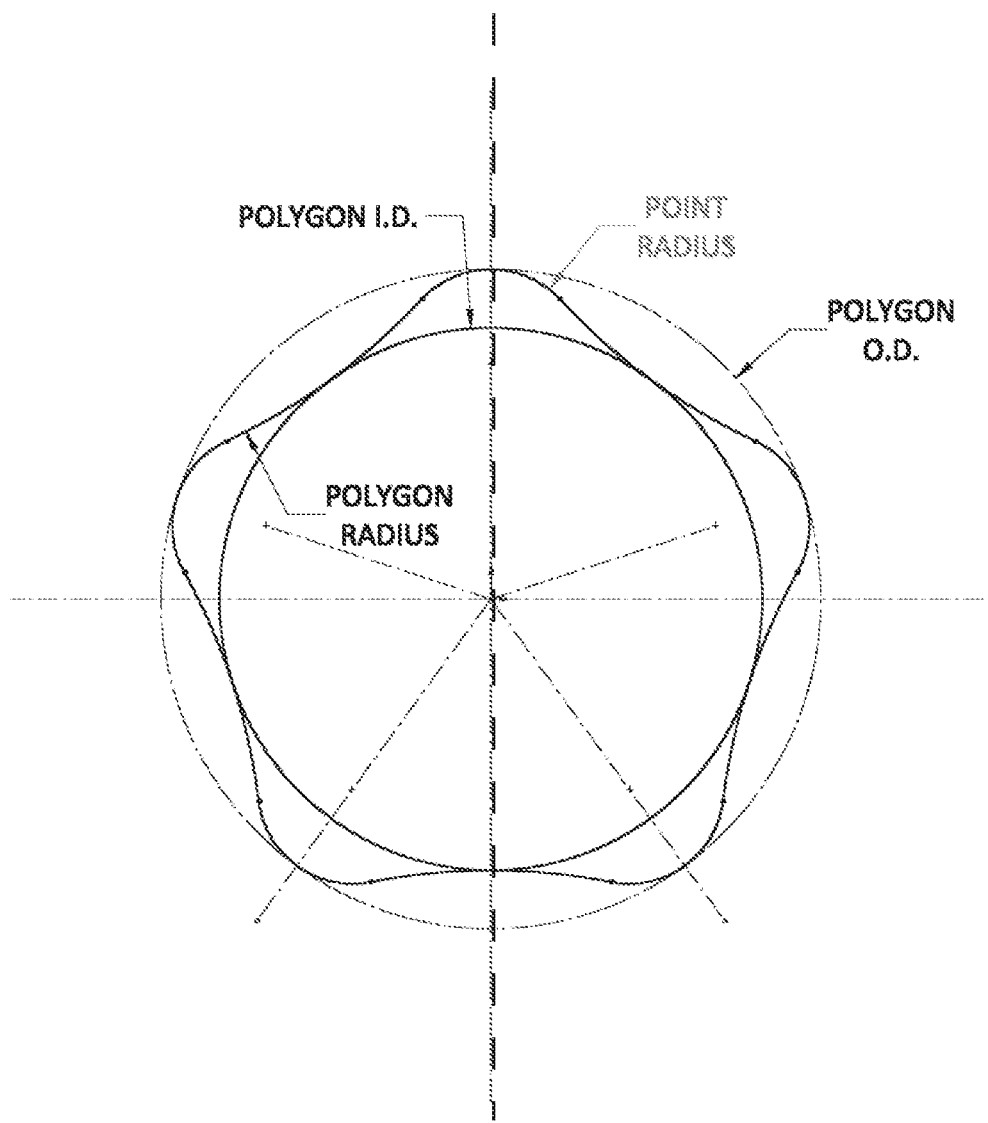
Figure 14A:
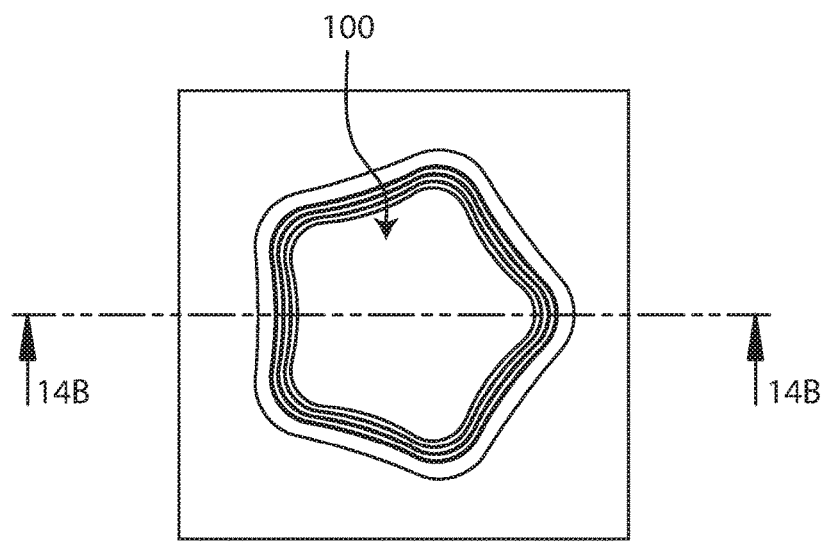
Figure 14B:
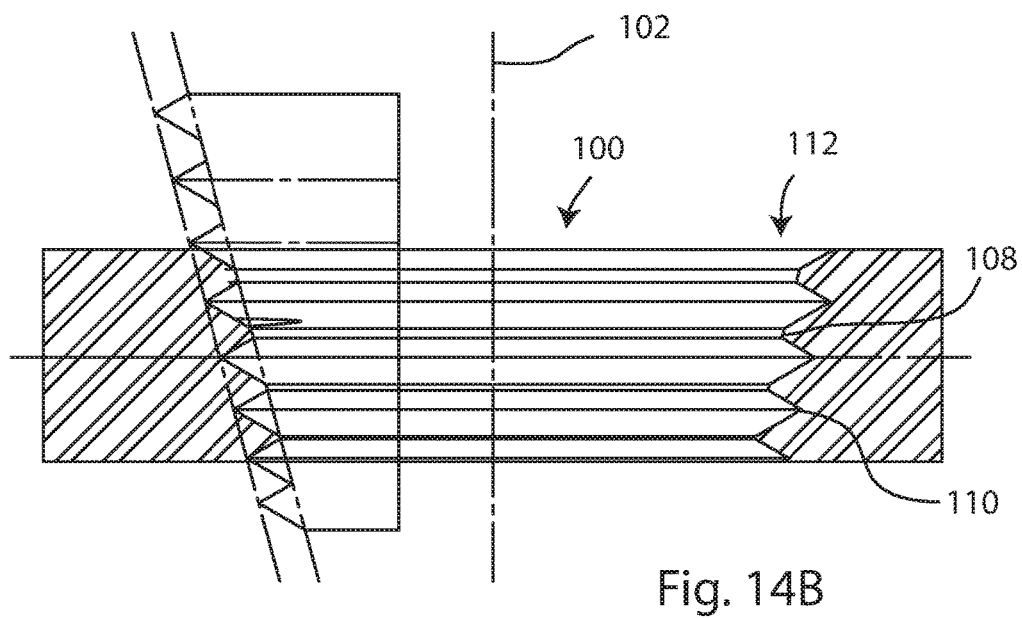
Figure 15A:
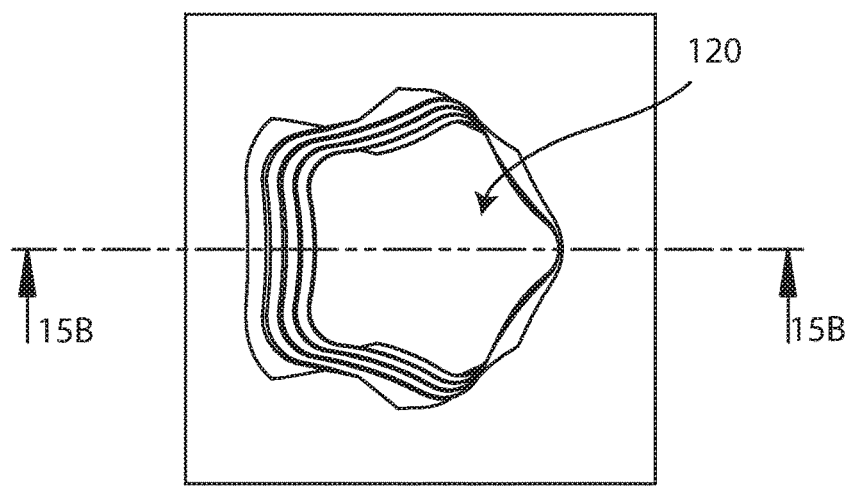
Figure 15B:
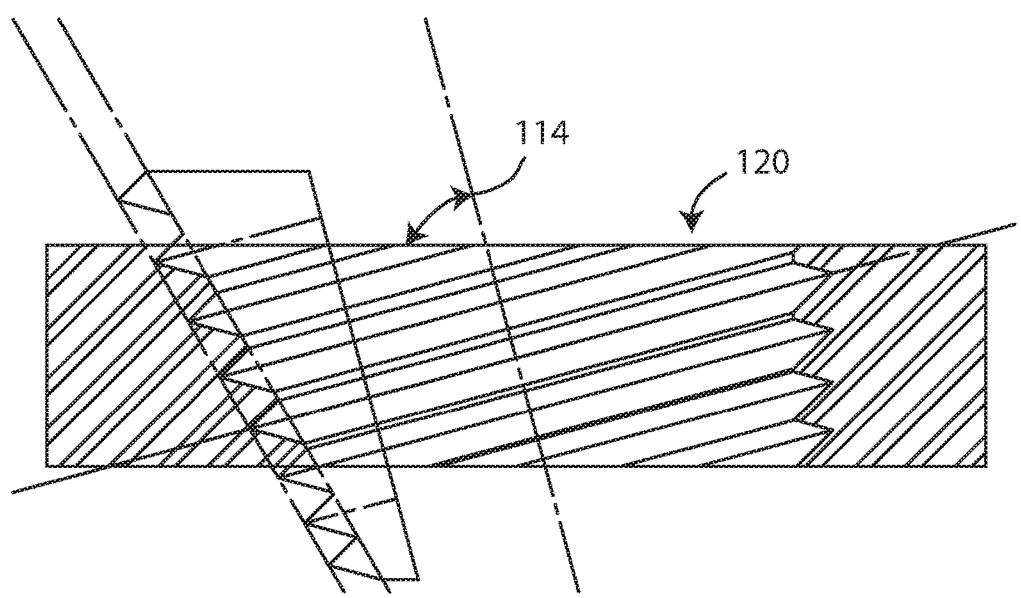
Figures 16A, 16B:
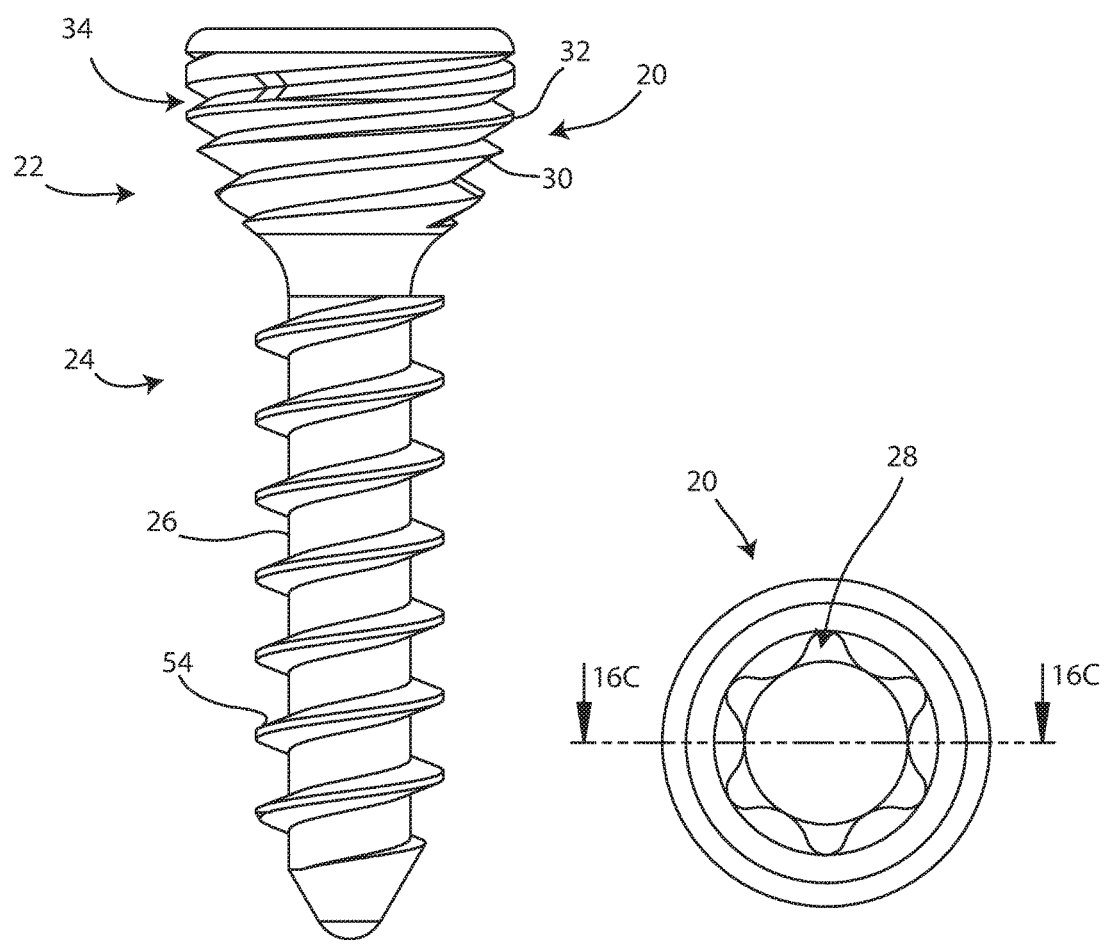
Figure 16C:
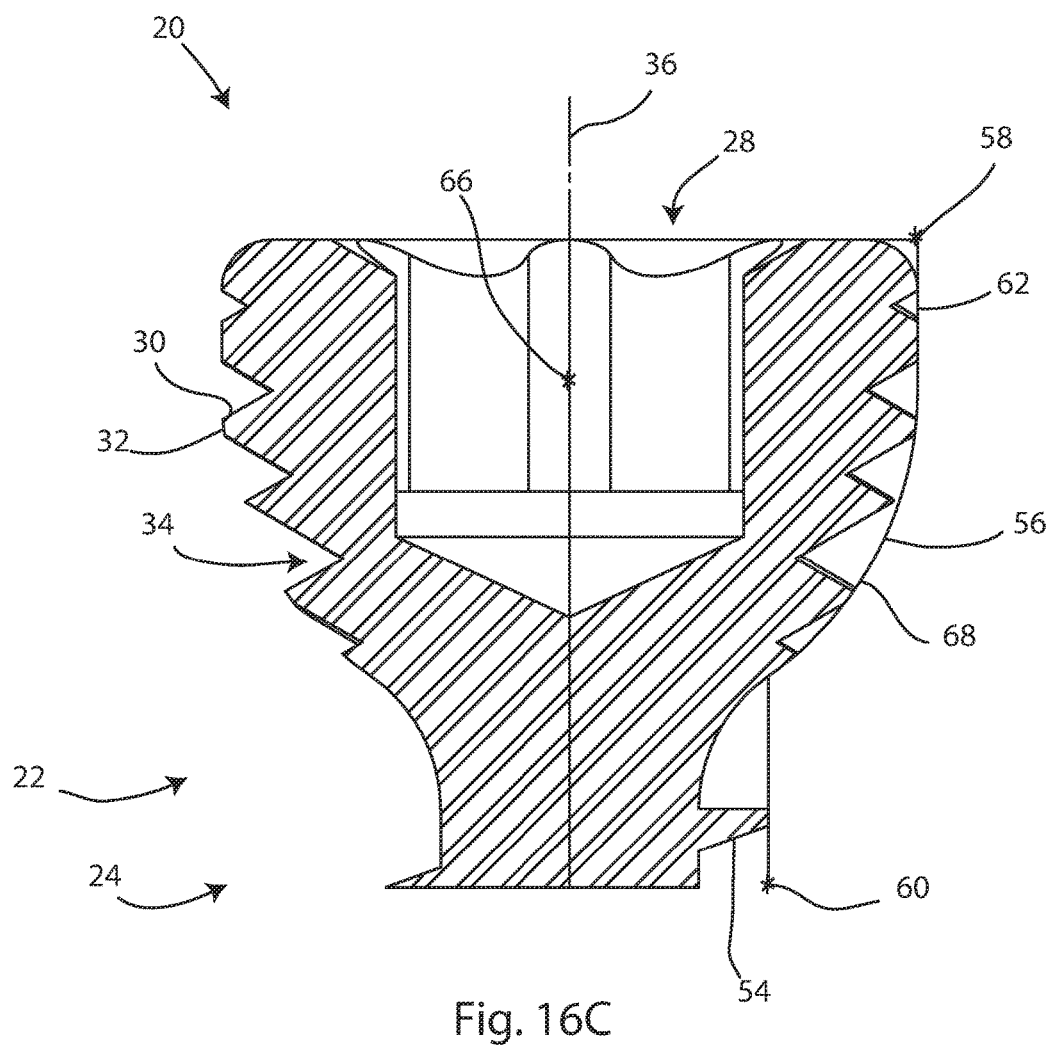
Figure 17A:
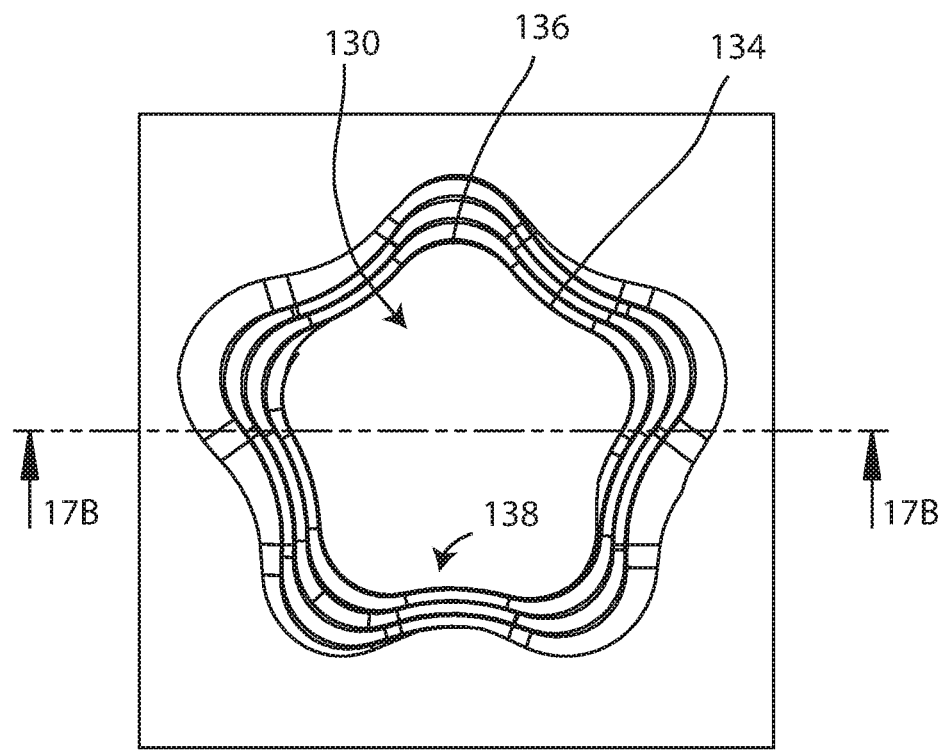
Figure 17B:
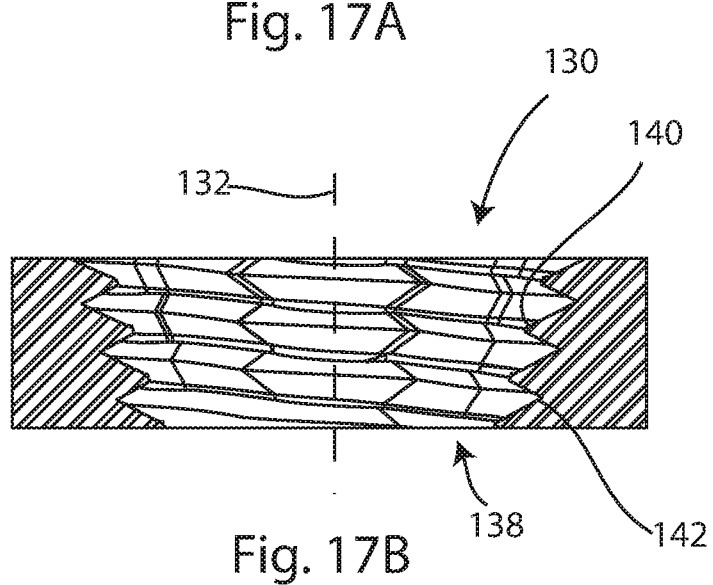
Figure 17C:
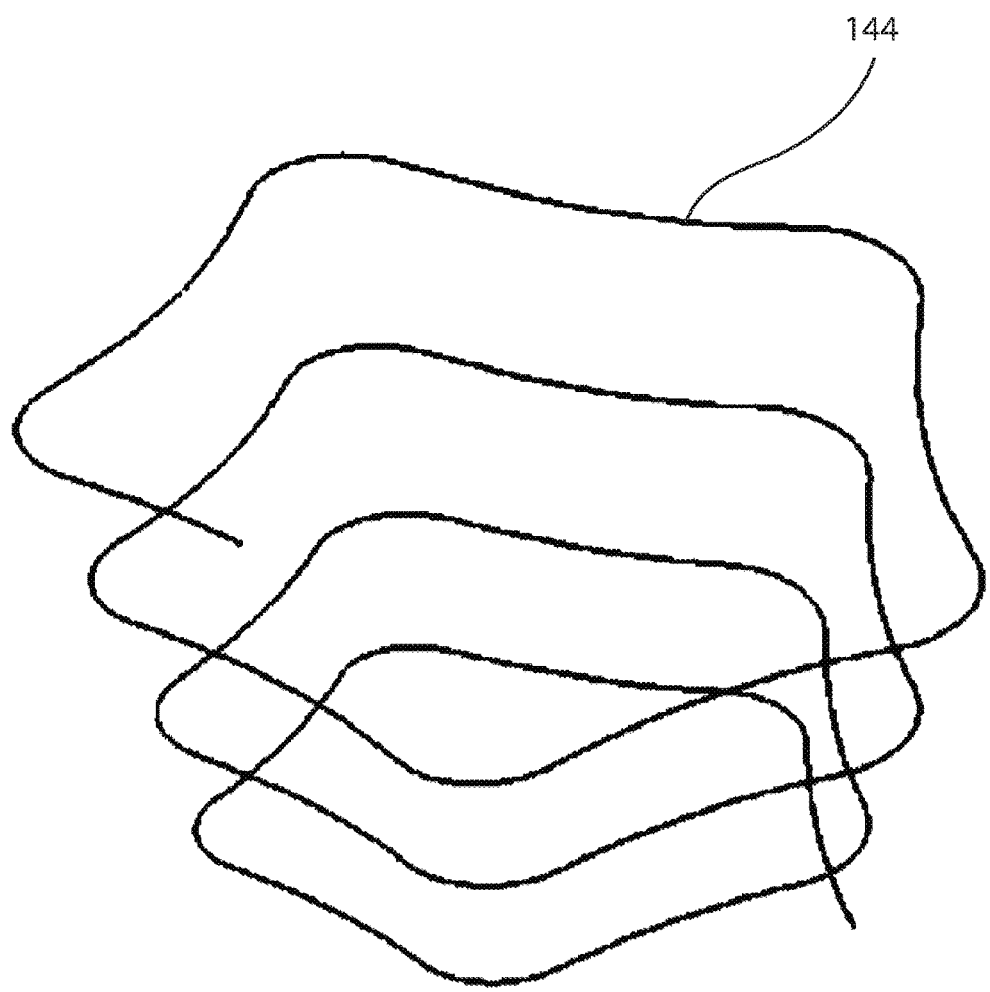
Figure 18A:
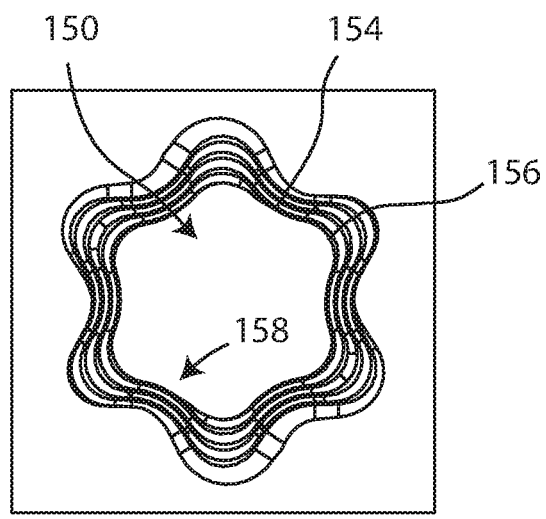
Figure 18B:
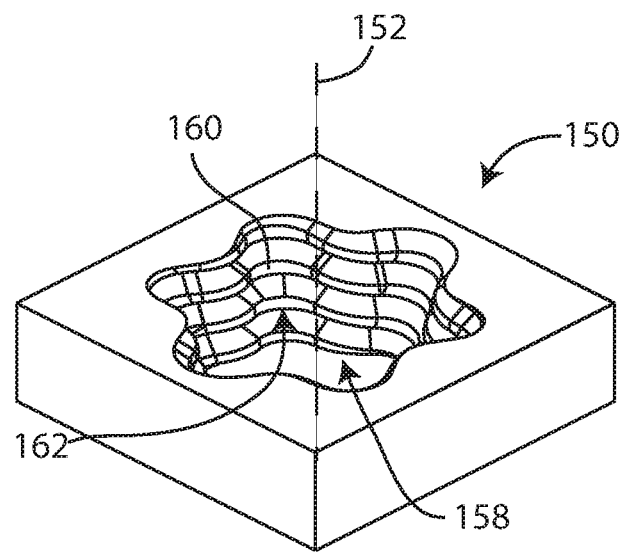
Figure 19A:
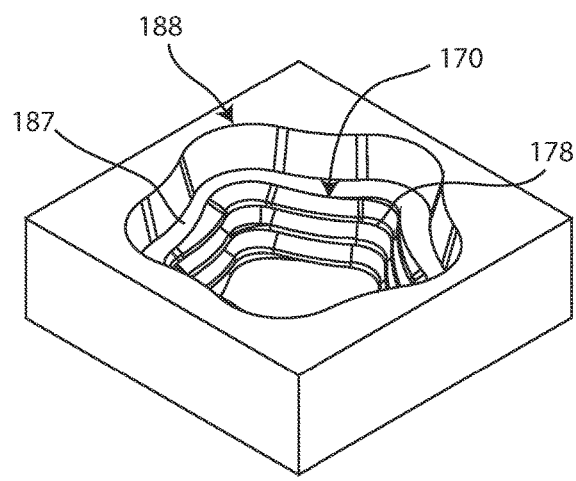
Figure 19B:
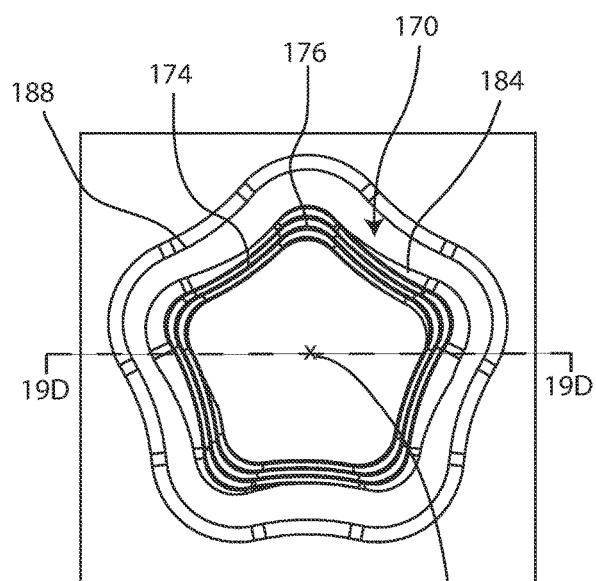
Figure 19C:
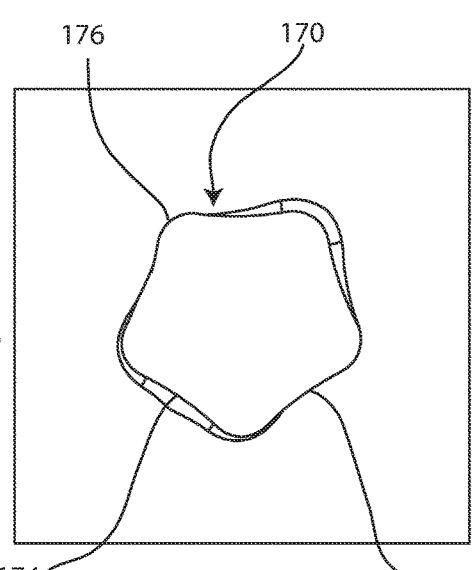
Figure 19D:
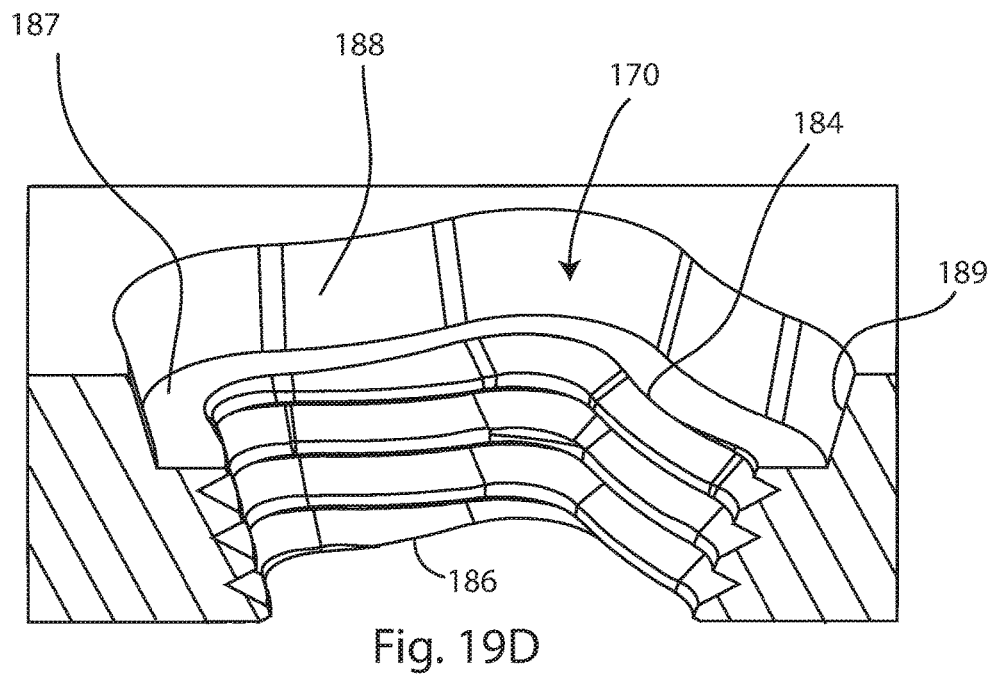
Figure 19E:
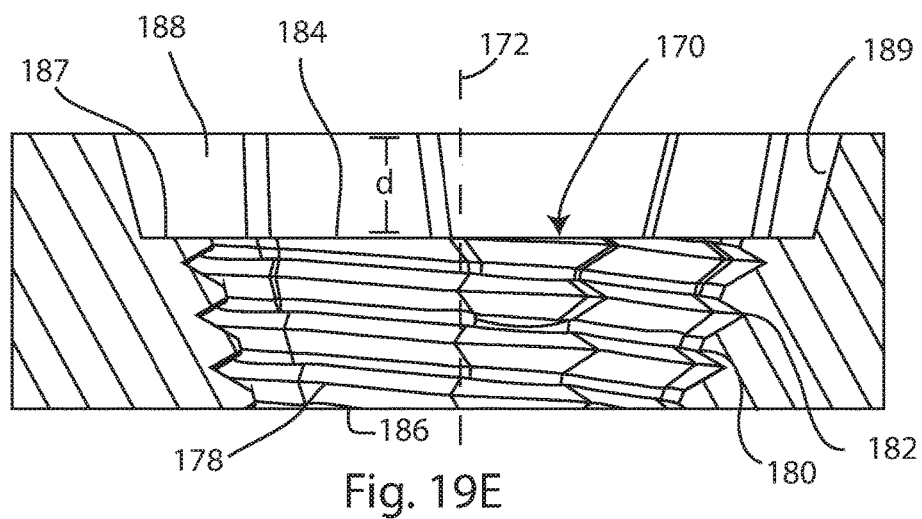
Figure 20D:
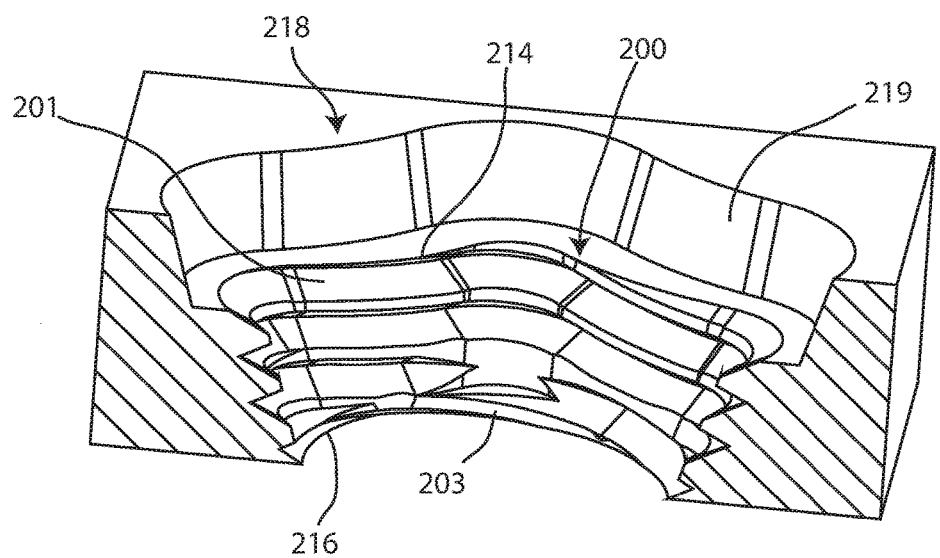
Figure 20E:
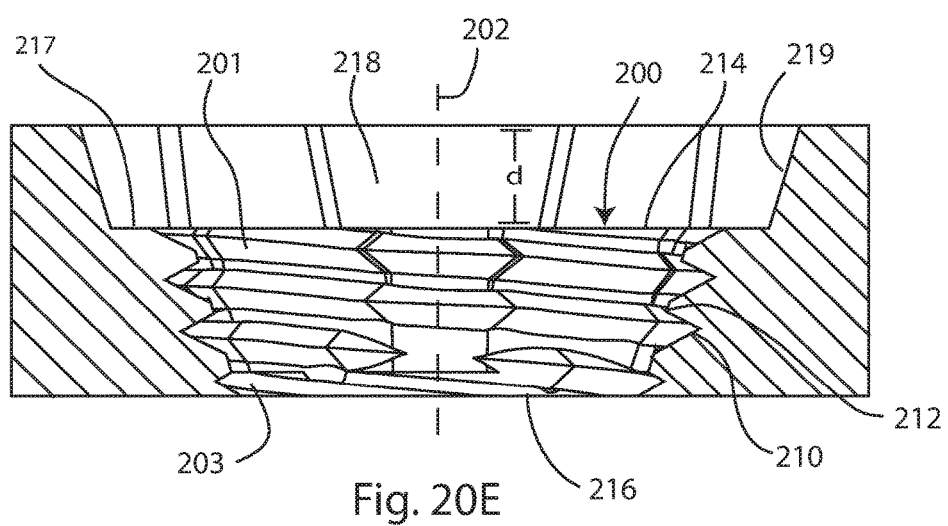
Figure 21D:
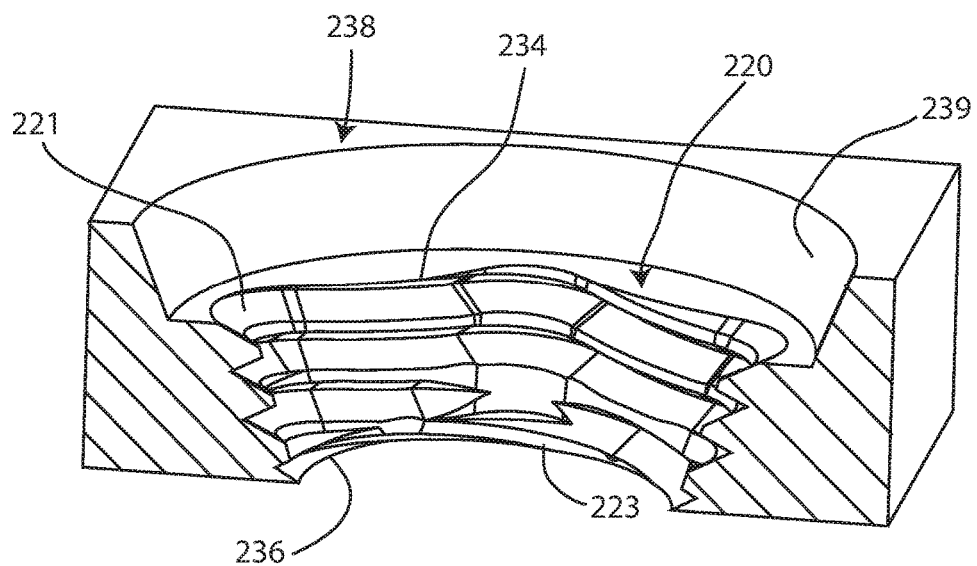
Figure 21E:
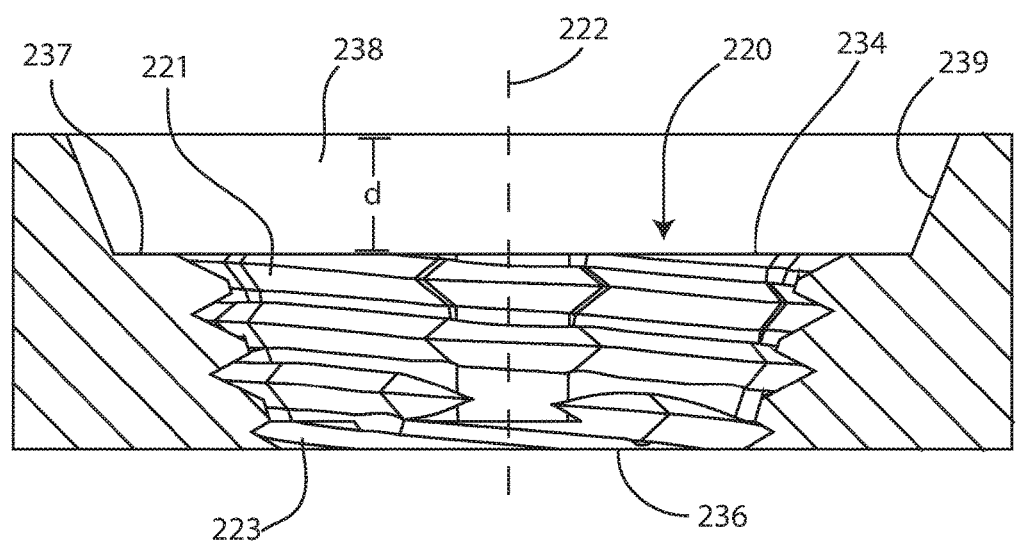
Figure 22A:
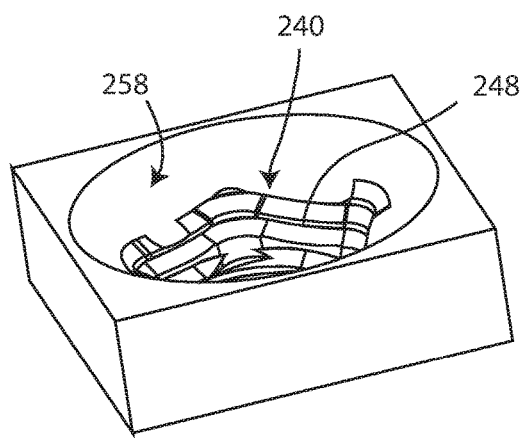
Figure 22B:
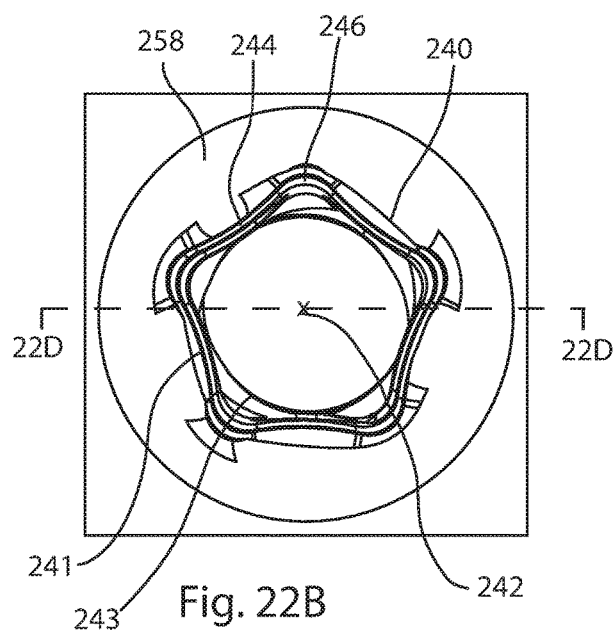
Figure 22C:
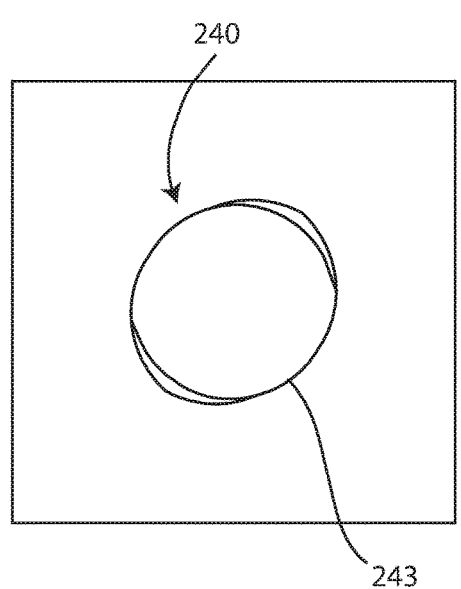
Figure 22D:
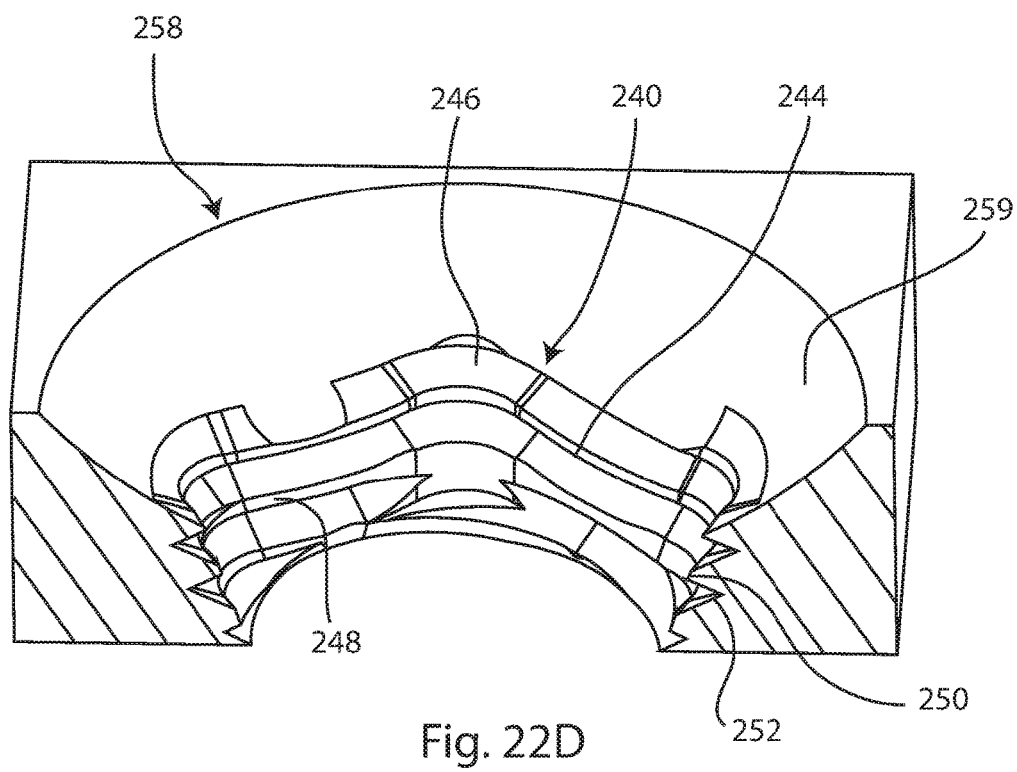
Figure 22E:
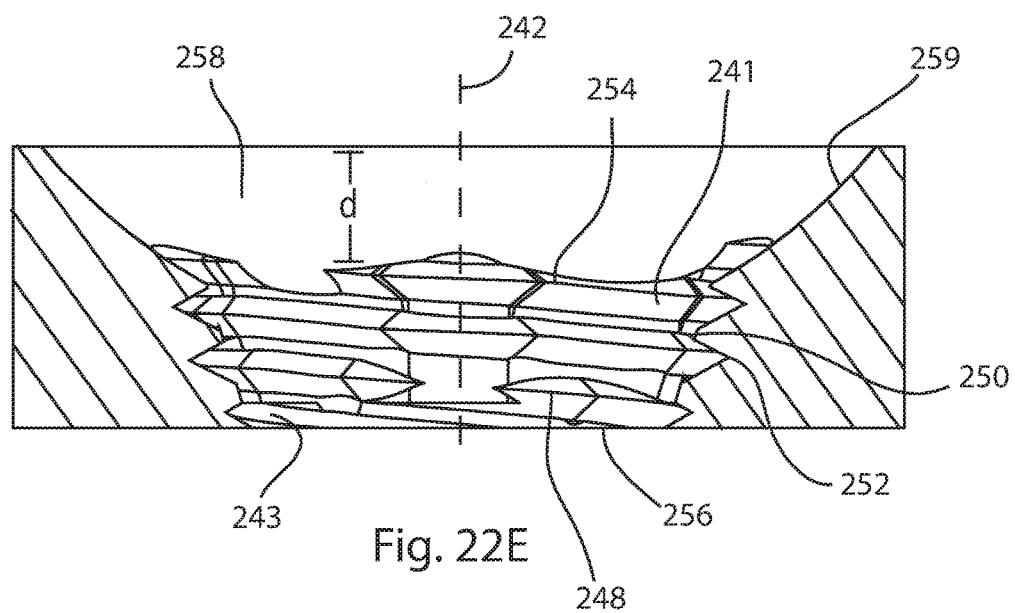
Figure 23D:
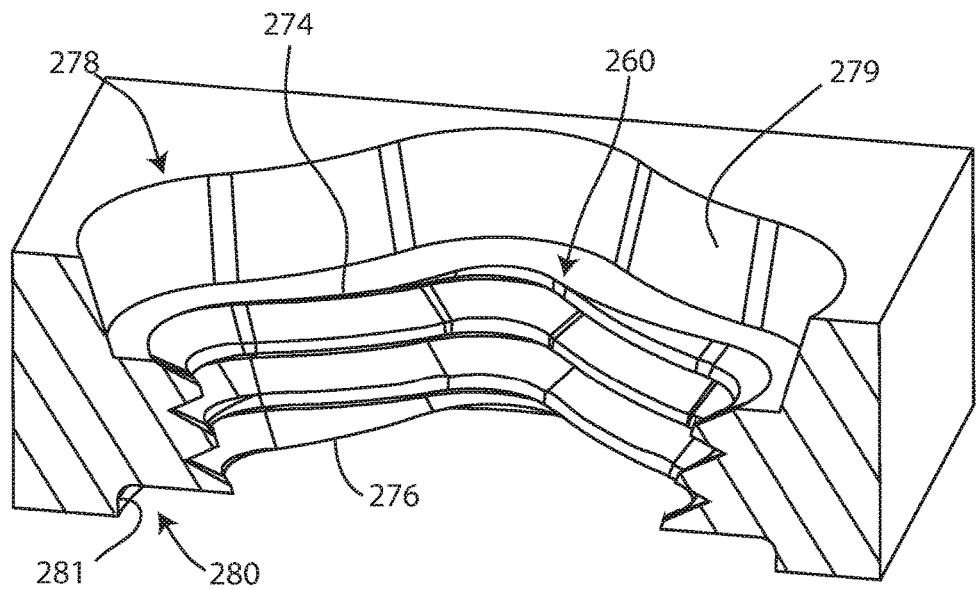
Figure 23E:
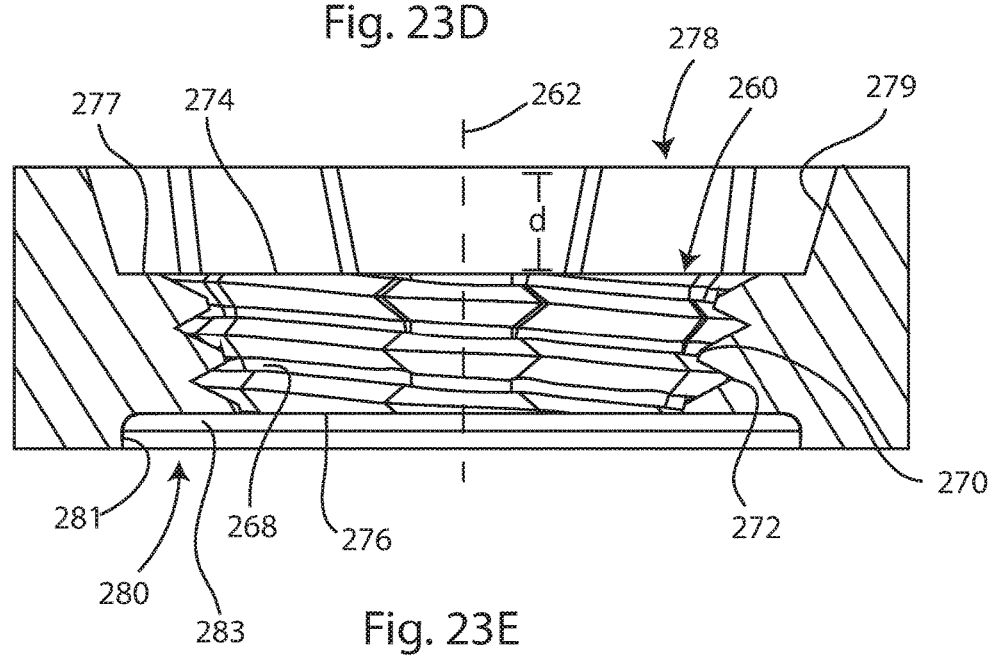
Figure 24D:
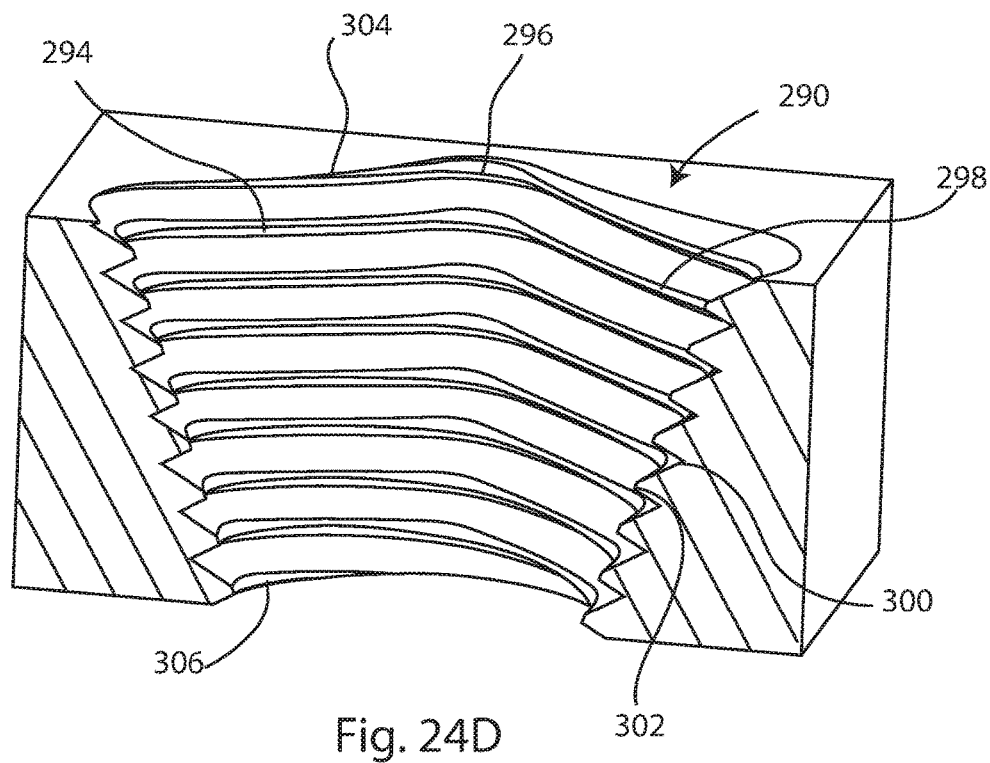
Figure 24E:
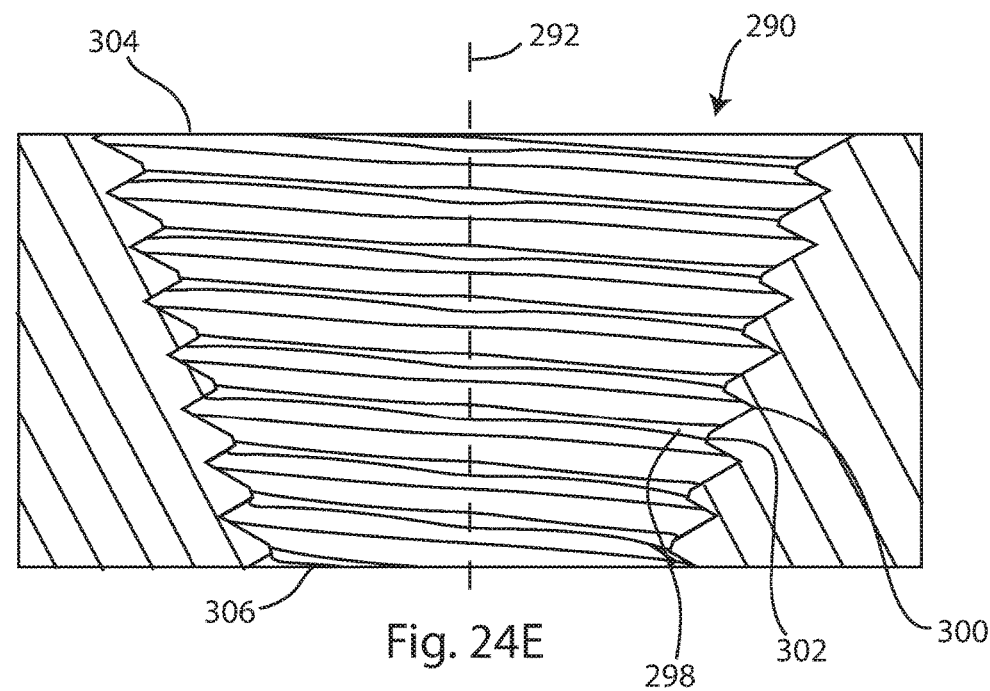
Figure 25D:
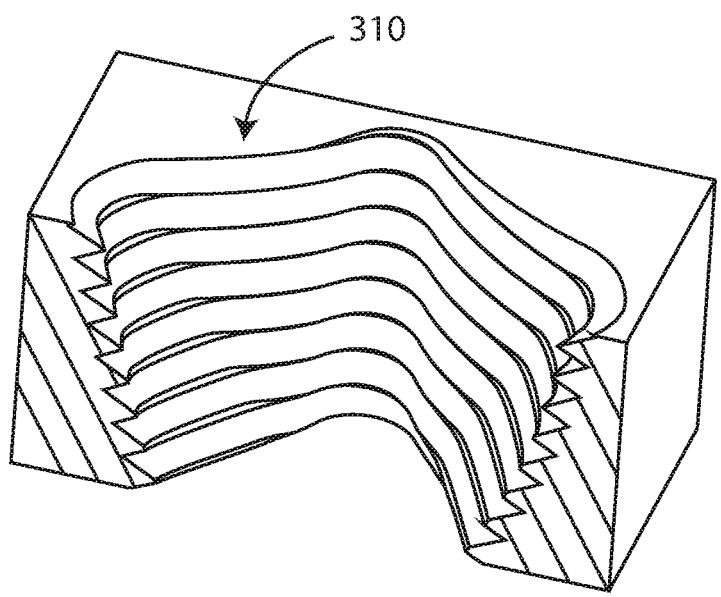
Figure 25E:
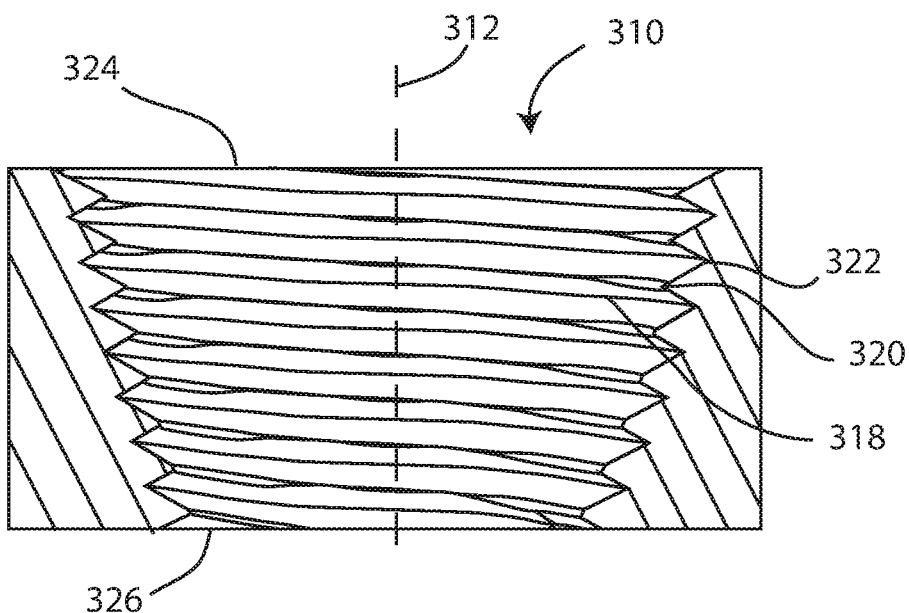
Figure 26A:
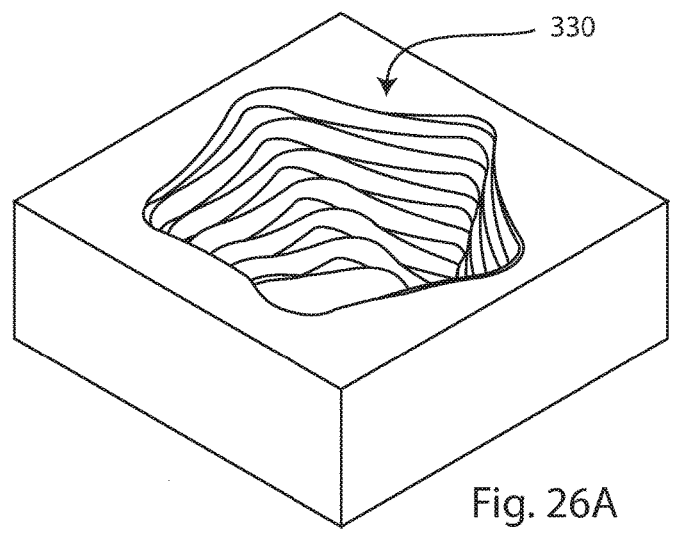
Figure 26B:
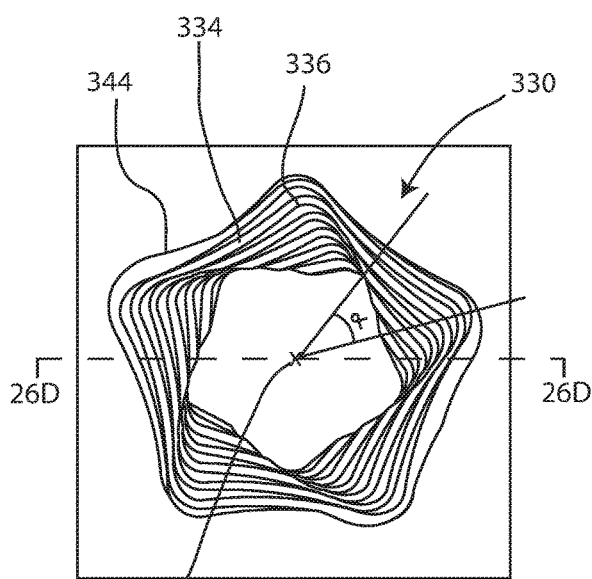
Figure 26C:
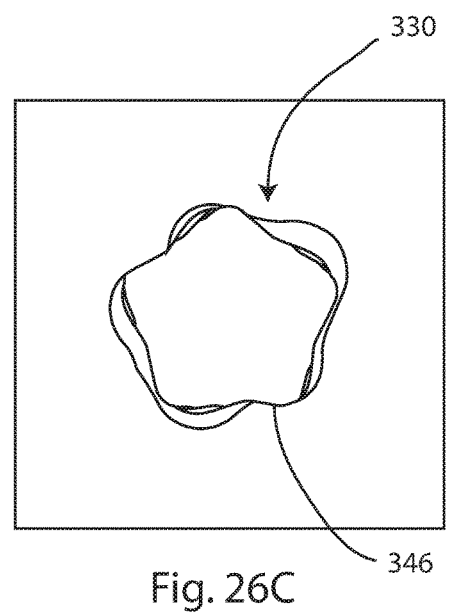
Figure 26D:
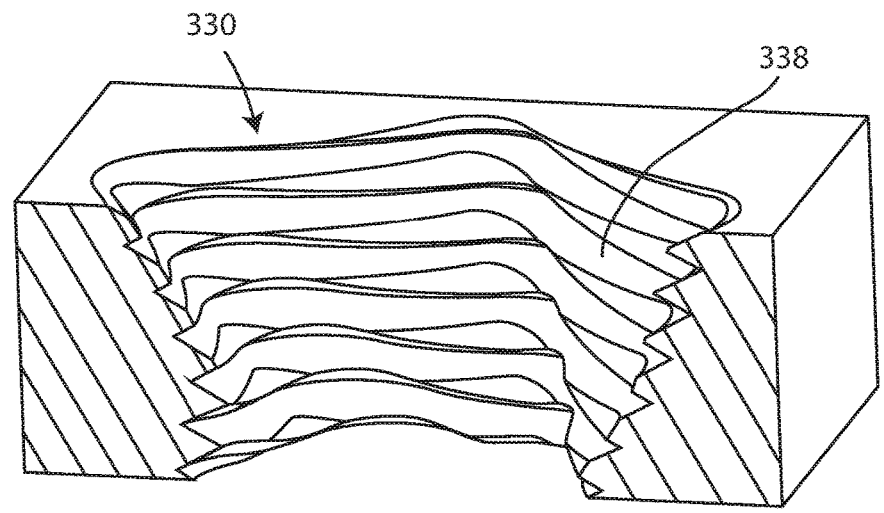
Figure 26E:
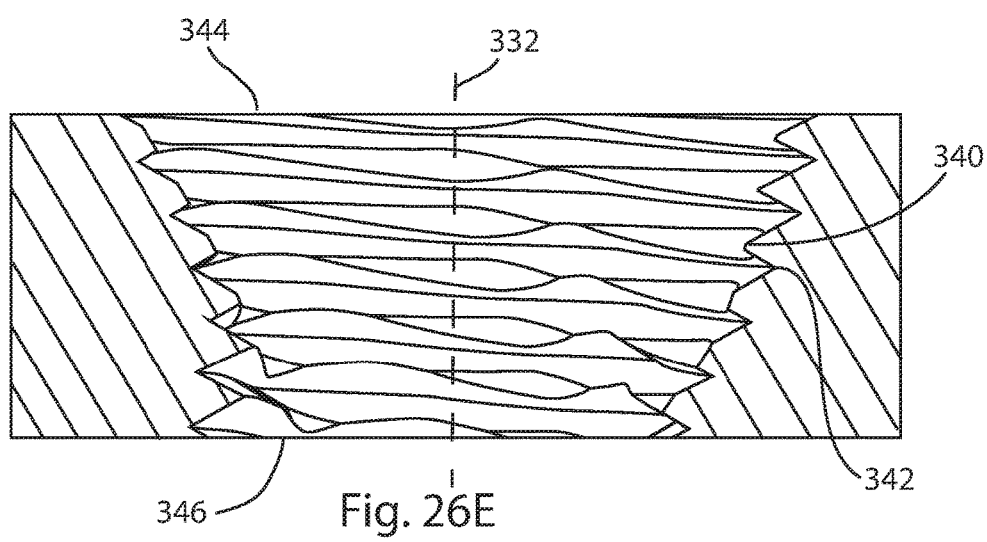
Figure 27A:
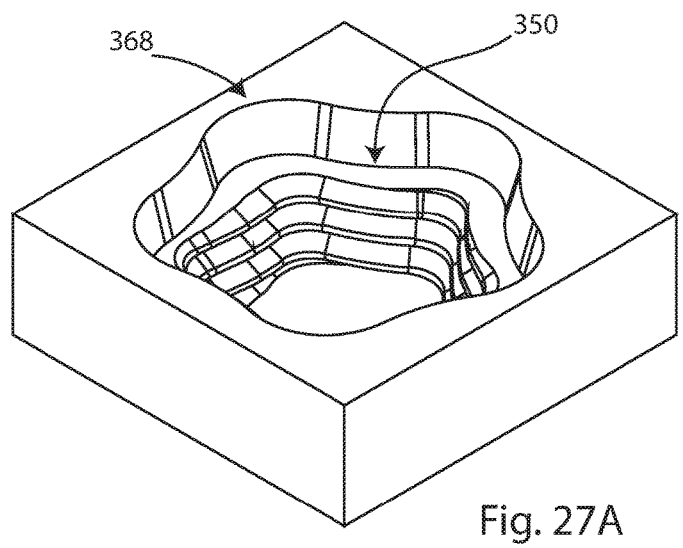
Figure 27B:
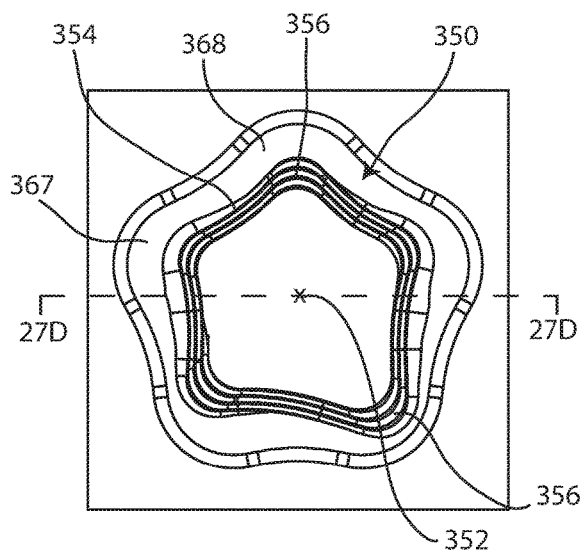
Figure 27C:
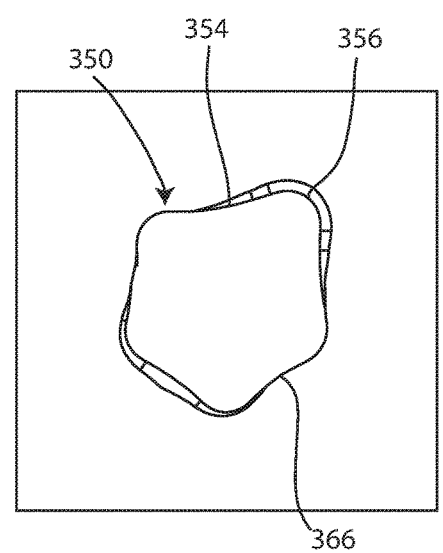
Figure 27D:
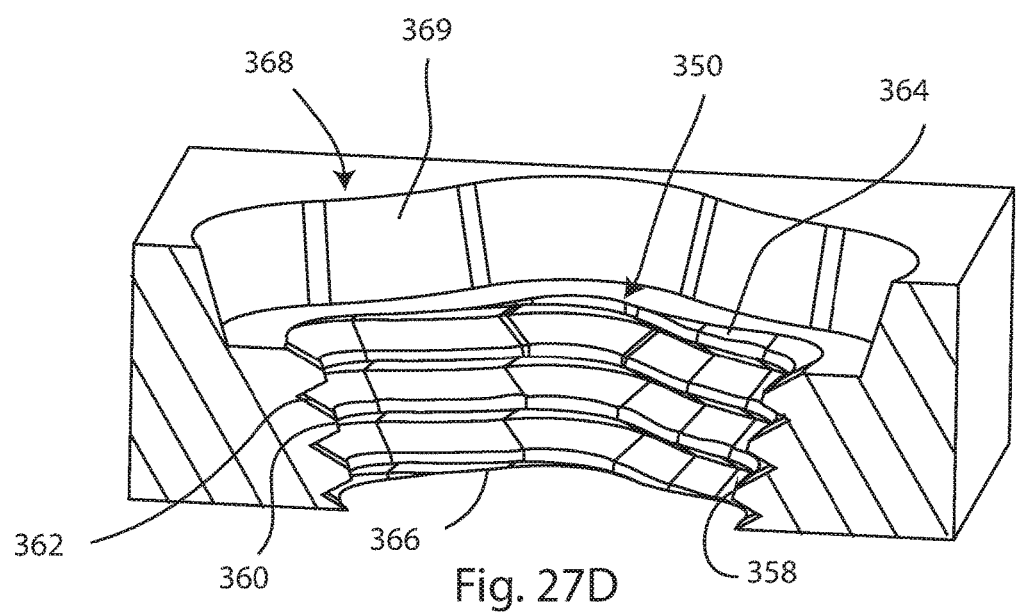
Figure 27E:
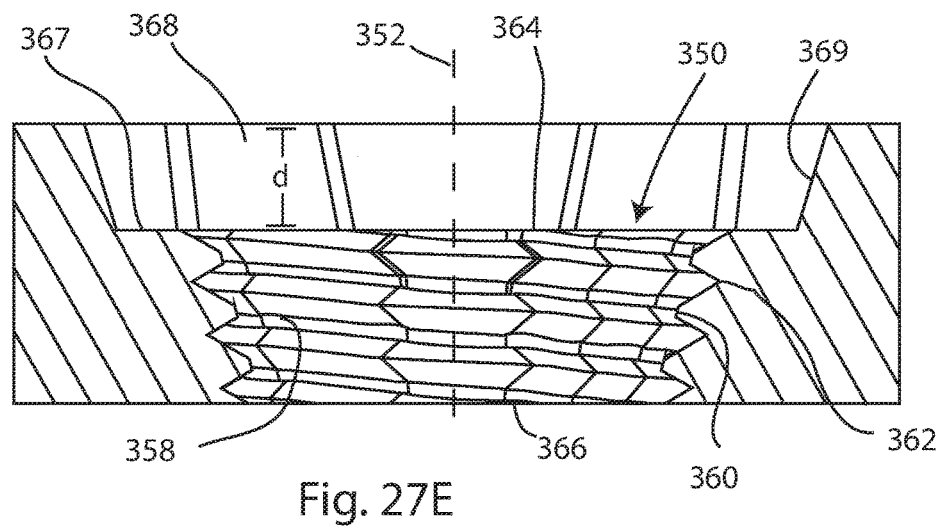
Figure 28D:
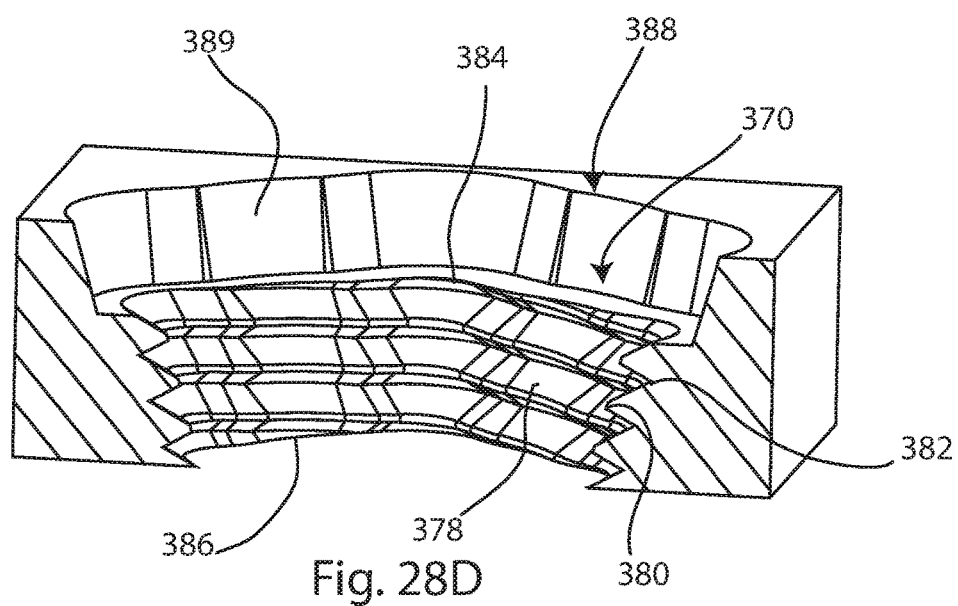
Figure 28E:
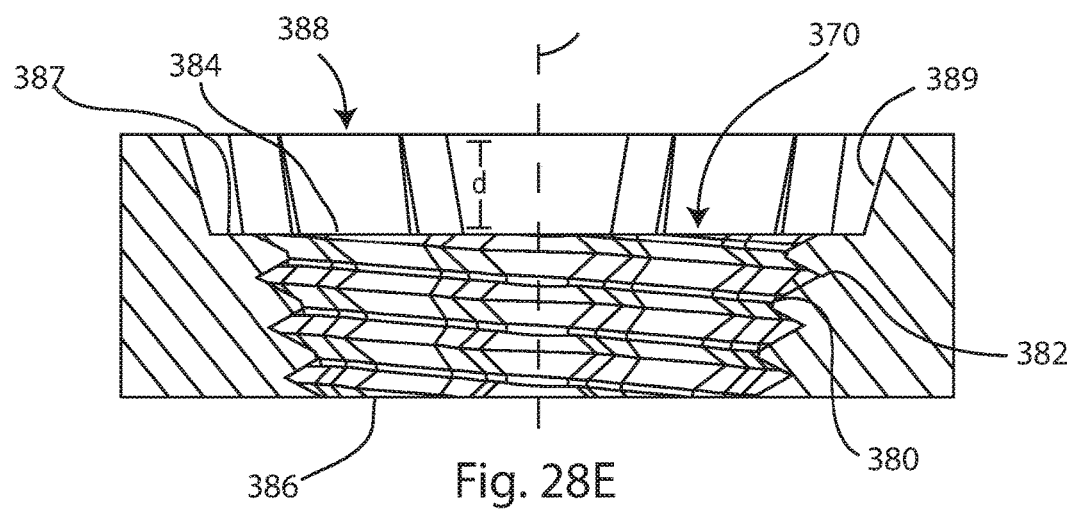

FIG. 1 is an isometric view of an interlocking interface between a screw and a socket;

FIG. 2 is an isometric exploded view of the screw and socket of FIG. 1;

FIG. 3 is a top view of the screw and socket of FIG. 1;

FIG. 4A is another top view of the screw and socket of FIG. 1; FIG. 4B is a front cross-sectional view of the screw and socket of FIG. 1, taken along section line 4B-4B of FIG. 4A, a range of positions of the screw relative to the socket is shown by dashed lines; and FIG. 4C is a front cross-sectional view of the socket of FIG. 1, also taken along section line 4B-4B of FIG. 4A;

FIG. 5 is a top view of the socket of FIG. 1;

FIG. 6 is an isometric view of another socket;

FIG. 7A is a top view of the socket of FIG. 6; and FIG. 7B is a front cross-sectional view of the socket of FIG. 6, taken along section line 7B-7B of FIG. 7A;

FIG. 8 is an isometric cross-sectional view of the socket of FIG. 6, taken along section line 7B-7B of FIG. 7A;

FIG. 9 is an isometric view of another interlocking interface between the screw and yet another socket;

FIG. 10 is an isometric exploded view of the screw and socket of FIG. 9;

FIG. 11A is a top view of the screw and socket of FIG. 9; and FIG. 11B is a compound front cross-sectional view of the screw and socket of FIG. 9, taken along section line 11B-11B of FIG. 11A, a first position of the screw shown on the left and a second position of the screw shown on the right;

FIG. 12 is a top view of the socket of FIG. 9;

FIG. 13 is a sketch of the cross-sectional geometry of the socket of FIG. 9;

FIG. 14A is another top view of the socket of FIG. 9; and FIG. 14B is a front cross-sectional view of the socket of FIG. 9, taken along section line 14B-14B of FIG. 11A;

FIG. 15A is a top view of yet another socket; and FIG. 15B is a front cross-sectional view of the socket of FIG. 15A, taken along section line 15B-15B of FIG. 15A;

FIG. 16A is a front view of the screw of FIG. 1; FIG. 16B is a top view of the screw of FIG. 1; and FIG. 16C is a front cross sectional view of the screw of FIG. 1, taken along section line 16C-16C of FIG. 16B;

FIG. 17A is a top view of yet another socket; FIG. 17B is a front cross-sectional view of the socket of FIG. 17A, taken along section line 17B-17B of FIG. 17A; and FIG. 17C is an isometric view of a sweep profile of the socket of FIG. 17A;

FIG. 18A is a top view of yet another socket; and FIG. 18B is an isometric view of the socket of FIG. 18A;

FIG. 19A is an isometric view of another socket and a counterbore; FIG. 19B is a top view of the socket and counterbore of FIG. 19A; FIG. 19C is a bottom view of the socket of FIG. 19A; FIG. 19D is an isometric cross-sectional view of the socket and counterbore of FIG. 19A, taken along section line 19D-19D of FIG. 19B; and FIG. 19E is a front cross-sectional view of the socket and counterbore of FIG. 19A, taken along section line 19D-19D of FIG. 19B;

FIG. 20A is an isometric view of another socket and a counterbore; FIG. 20B is a top view of the socket and counterbore of FIG. 20A; FIG. 20C is a bottom view of the socket of FIG. 20A; FIG. 20D is an isometric cross-sectional view of the socket and counterbore of FIG. 20A, taken along section line 20D-20D of FIG. 20B; and FIG. 20E is a front cross-sectional view of the socket and counterbore of FIG. 20A, taken along section line 20D-20D of FIG. 20B;

FIG. 21A is an isometric view of another socket and a counterbore; FIG. 21B is a top view of the socket and counterbore of FIG. 21A; FIG. 21C is a bottom view of the socket of FIG. 21A; FIG. 21D is an isometric cross-sectional view of the socket and counterbore of FIG. 21A, taken along section line 21D-21D of FIG. 21B; and FIG. 21E is a front cross-sectional view of the socket and counterbore of FIG. 21A, taken along section line 21D-21D of FIG. 21B;

FIG. 22A is an isometric view of another socket and a counterbore; FIG. 22B is a top view of the socket and counterbore of FIG. 22A; FIG. 22C is a bottom view of the socket of FIG. 22A; FIG. 22D is an isometric cross-sectional view of the socket and counterbore of FIG. 22A, taken along section line 22D-22D of FIG. 22B; and FIG. 22E is a front cross-sectional view of the socket and counterbore of FIG. 22A, taken along section line 22D-22D of FIG. 22B;

FIG. 23A is an isometric view of another socket and two counterbores; FIG. 23B is a top view of the socket and counterbores of FIG. 23A; FIG. 23C is a bottom view of the socket of FIG. 23A; FIG. 23D is an isometric cross-sectional view of the socket and counterbores of FIG. 23A, taken along section line 23D-23D of FIG. 23B; and FIG. 23E is a front cross-sectional view of the socket and counterbores of FIG. 23A, taken along section line 23D-23D of FIG. 23B;

FIG. 24A is an isometric view of another socket; FIG. 24B is a top view of the socket of FIG. 24A; FIG. 24C is a bottom view of the socket of FIG. 24A; FIG. 24D is an isometric cross-sectional view of the socket of FIG. 24A, taken along section line 24D-24D of FIG. 24B; and FIG. 24E is a front cross-sectional view of the socket of FIG. 24A, taken along section line 24D-24D of FIG. 24B;

FIG. 25A is an isometric view of another socket; FIG. 25B is a top view of the socket of FIG. 25A; FIG. 25C is a bottom view of the socket of FIG. 25A; FIG. 25D is an isometric cross-sectional view of the socket of FIG. 25A, taken along section line 25D-25D of FIG. 25B; and FIG. 25E is a front cross-sectional view of the socket of FIG. 25A, taken along section line 25D-25D of FIG. 25B;

FIG. 26A is an isometric view of another socket; FIG. 26B is a top view of the socket of FIG. 26A; FIG. 26C is a bottom view of the socket of FIG. 26A; FIG. 26D is an isometric cross-sectional view of the socket of FIG. 26A, taken along section line 26D-26D of FIG. 26B; and FIG. 26E is a front cross-sectional view of the socket of FIG. 26A, taken along section line 26D-26D of FIG. 26B;

FIG. 27A is an isometric view of another socket and a counterbore; FIG. 27B is a top view of the socket and counterbore of FIG. 27A; FIG. 27C is a bottom view of the socket of FIG. 27A; FIG. 27D is an isometric cross-sectional view of the socket and counterbore of FIG. 27A, taken along section line 27D-27D of FIG. 27B; and FIG. 27E is a front cross-sectional view of the socket and counterbore of FIG. 27A, taken along section line 27D-27D of FIG. 27B; and FIG. 28A is an isometric view of another socket and a counterbore; FIG. 28B is a top view of the socket and counterbore of FIG. 28A; FIG. 28C is a bottom view of the socket of FIG. 28A; FIG. 28D is an isometric cross-sectional view of the socket and counterbore of FIG. 28A, taken along section line 28D-28D of FIG. 28B; and FIG. 28E is a front cross-sectional view of the socket and counterbore of FIG. 28A, taken along section line 28D-28D of FIG. 28B.

DETAILED DESCRIPTION

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

Referring to FIGS. 1-5, a locking interface 10 includes a head 20 and a socket 40.

With reference to FIGS. 1-5 and 16A-16C, the head 20 is an external feature which may be formed on any medical device component, such as a fastener, connector, rod, link, bone-contacting component, articular component, and the like. The head 20 shown in FIG. 1 is an external feature formed on a proximal end 22 of a fastener 24. The fastener 24 includes a distal portion 26 which may include bone fixation features, such as external threads, ribs, porous coating, and the like; however, for simplicity, a smooth cylindrical distal portion 26 is shown in FIGS. 1-2, and 4B; a distal portion 26 with an external thread 54 is shown in FIGS. 16A and 16C. The head 20 may include an instrument connection feature 28. The instrument connection feature 28 may be an internal or external feature; a hexagonal internal feature is shown in FIGS. 1-4A and a hexalobular internal feature is shown in FIG. 16B. The internal feature may be a slot, a cruciform indentation or Phillips socket, a polygonal indentation, a hexalobular or Torx socket, a circular hole, and the like. Any of these features may be expressed as an external feature as well. The instrument connection feature 28 may be shaped and sized for complementary connection with an instrument (not shown). The connection feature 28 may couple the head 20 to an instrument so that compressive, tensile, torque, and/or other forces may be transmitted between the head 20 and the instrument. The connection may be a slip fit, a line-to-line fit, an interference fit, an interlocking undercut fit, threads, a snap fit, a taper fit, or any other connection.

Referring to FIG. 16C, the head 20 may be formed by revolving a profile 56 about a longitudinal axis of revolution 36, which may also be described as a longitudinal axis 36 of the head 20. The revolved profile 56 may be formed by one or more lines, curves, or other two-dimensional shapes. The head 20 may be cylindrical, multi-cylindrical, frustoconical, multi-conical, spherical, cylindro-spherical, ovoid, and the like. The head 20 may also have a faceted perimeter. In the example shown in FIG. 16C, the revolved profile 56 of the head 20 extends at least between a proximal point 58 and a distal point 60 to define an outermost shape of the head 20. The illustrated profile 56 includes a proximal line segment 62 which is parallel to the axis 36, and a distal arc segment 68 which is tangent to the line segment 62. A center point 66 of the arc segment 68 may lie on the axis 36 as shown or may be offset from the axis 36. When revolved about the axis 36, arc segment 68 forms a spherical portion of the head 20 by virtue of having center point 66 on the axis 36.

The head 20 includes external corrugations 30 which may be described as forming alternating peaks 32 and valleys 34. The corrugations 30 may be formed in the head 20 so that the peaks 32 lie upon, or follow, the surface of the head. The valleys 34 may also follow the surface of the head at a fixed offset so that there is a constant valley depth. Alternately, the valleys 34 may follow at a variable offset, so that valley depth varies along the head. The peaks 32 and/or valleys 34 may be sharp or blunt. The external corrugations 30 may be intact or uninterrupted throughout their extent along the head 20.

The socket 40 is a noncircular hole, such as the rounded rectangular hole illustrated in FIGS. 1-5. The socket 40 may have a longitudinal axis 52. The socket 40 may be formed in any medical device component, such as a plate, washer, rod, link, bone-contacting component, articular component, and the like. The socket 40 may extend completely through a component, or only partially through the component. The socket 40 may be multi-sided; the example of FIGS. 1-5 has four flat sides 42 and four rounded corners 44. The socket 40 may include two or more sides in a polygonal arrangement, such as an oval, triangle, rectangle, pentagon, hexagon, heptagon, octagon, and so on. In this specification, a polygon may have sides that deviate from perfectly straight, for example by bulging or bending inward or outward. The corners 44 may be sharp or rounded. In other examples, the socket 40 may have a poly-lobular profile such as a starburst shape with three or more points or corners 44. The points 44 may be sharp or rounded, and the sides 42 may bulge toward the interior of the socket in these examples. Examples of poly-lobular profile profiles include pentagram, hexalobe, hexagram, and other star-shaped shapes. Another example may be described as a spline. The socket 40 may have a constant cross-sectional geometry over the full depth of the socket 40, as seen best in FIG. 4B. Alternatively, the socket 40 may taper or bulge along its length. The socket 40 may have a spherical or partial spherical interior. The socket 40 may twist along its depth.

The socket 40 includes an internal corrugation 46 which includes alternating peaks 48 and valleys 50 along the depth of the socket 40, or a portion thereof. The peaks 48 and/or valleys 50 may be sharp or blunt. The peaks 48 may lie upon, or follow, the interior surface of the socket 40. The valleys 50 may be described as indentations into the interior surface of the socket 40, and thus the valleys 50 may also follow the interior surface of the socket 40, albeit offset below the interior surface. The valleys 50 may follow the interior surface exactly with a constant offset, or generally, with a variable offset. The internal corrugation 46 may be intact, or uninterrupted, throughout its extent so that all of the peaks 48 and valleys 50 are intact. This configuration may reduce socket stresses compared to designs with interrupted threads or other discrete protrusions in the socket.

The internal corrugations 46 may be formed by a single indentation, or valley 50, which winds around the socket 40 while progressing longitudinally within the socket 40. This arrangement is best seen in FIG. 2. More than one indentation may be present. Additional indentations may wind around the socket 40 with the single indentation. The longitudinal progression per circuit around the socket 40 may be constant or variable.

In use, the head 20 may be inserted into the socket 40 with the axes 36, 52 aligned or coaxial. This arrangement is shown in FIGS. 1-2 and in FIG. 4B in solid lines. The external corrugations 30 of the head 20 may engage with the internal corrugation feature 46 of the socket 40 so that the peaks 32 rest in the valleys 50 and the peaks 48 rest in the valleys 34. This engagement may resemble a traditional threaded engagement. However, the incongruent shapes of the head 20 and socket 40 provide alternating zones of contact and clearance between the head 20 and the socket 40, as can be seen best in FIG. 3 with reference to FIG. 5. Contact occurs between the sides 42 and the head 20, and clearance occurs between the corners 44 and the head 20.

In another method of use, the head 20 may be inserted into the socket 40 with the axes 36, 52 misaligned. The axes 36, 52 may be intentionally or unintentionally misaligned. Two examples of this arrangement are shown in FIG. 4B in dashed lines. The external corrugations 30 of the head 20 may engage with the internal corrugation feature 46 of the socket 40 to lock the head 20 at a range of angles with respect to the socket 40. This arrangement is facilitated by the zones of contact and clearance between the head 20 and the socket 40, which permit the corrugations 30 to skip over a zone of clearance instead of encountering an interfering peak 48 in the socket. The dashed line representations in FIG. 4B show two possible angular orientations of the head 20 with respect to the socket 40 out of a range of possible angular orientations extending in a conical field around the axis 52 of the socket 40. The locking interconnection between the head 20 and the socket 40 may be described as polyaxial for this reason.

FIGS. 6-8 show another socket 70 for use with the head 20 in a polyaxial locking interconnection. Socket 70 is another noncircular hole, which may have a longitudinal axis 72. The socket 70 may be formed in any medical device component, such as a plate, washer, rod, link, bone-contacting component, articular component, and the like. The socket 70 may extend completely through a component, or only partially through the component. The socket 70 may include two or more sides in a polygonal or poly-lobular arrangement. The socket 70 may have six flat sides 74 and six rounded corners 76, however the corners 76 may be sharp instead. The socket 70 may have a constant cross-sectional geometry over the full depth of the socket 70 as seen best in FIG. 7B. Alternatively, the socket 70 may taper or bulge along its length. The socket 70 may have a spherical or partial spherical interior. The socket 70 may twist along its depth.

The socket 70 includes an internal corrugation 78 which includes alternating peaks 80 and valleys 82 along the depth of the socket 70, or a portion thereof. The peaks 80 and/or valleys 82 may be sharp or blunt. The peaks 80 may lie upon, or follow, the interior surface of the socket 70. The valleys 82 may be described as indentations into the interior surface of the socket 70, and thus the valleys 82 may also follow the interior surface of the socket 70, albeit offset below the interior surface. The valleys 82 may follow the interior surface exactly with a constant offset, or generally, with a variable offset. The internal corrugation 78 may be intact, or uninterrupted, throughout its extent so that all of the peaks 80 and valleys 82 are intact to minimize stress concentrations.

The internal corrugations 78 may be formed by a single indentation, or valley 82, which winds around the socket 70 while progressing longitudinally within the socket 70. This arrangement is best seen in FIG. 7B. More than one indentation may be present. Additional indentations may wind around the socket 70 with the single indentation. The longitudinal progression per circuit around the socket 70 may be constant or variable.

In use, the head 20 may be inserted into the socket 70 with the axes 36, 72 aligned or coaxial, or misaligned, as described above for socket 40. In either arrangement, the external corrugations 30 of the head 20 may engage with the internal corrugation feature 78 of the socket 70 to lock the head 20 at a range of angles with respect to the socket 70. The incongruent shapes of the head 20 and socket 70 provide alternating zones of contact and clearance between the head 20 and the socket 70. Contact occurs between the sides 74 and the head 20, and clearance occurs between the corners 76 and the head 20.

FIGS. 9-14B show another locking interface 90, which includes the head 20 and yet another socket 100. Socket 100 is another noncircular hole, which may have a longitudinal axis 102. The socket 100 may be formed in any medical device component, such as a plate, washer, rod, link, bone-contacting component, articular component, and the like. The socket 100 may extend completely through a component, or only partially through the component. The socket 100 may include two or more sides in a polygonal or poly-lobular arrangement. The socket 100 may have five sides 104 and five rounded corners 106, however the corners 106 may be sharp instead. The sides 104 may bulge slightly toward the interior of the socket 100. FIG. 13 shows a sketch depicting the geometry used to define the five-sided socket 100. The other sockets disclosed herein may employ similar sketches. The socket 100 may have a constant cross-sectional geometry over the full depth of the socket 100. Alternatively, the socket 100 may taper (FIGS. 11B and 14B) or bulge along its length. The socket 100 may have a spherical or partial spherical interior. The socket 100 may twist along its depth.

The socket 100 includes an internal corrugation 112 which includes alternating peaks 108 and valleys 110 along the depth of the socket 100, or a portion thereof. The peaks 108 and/or valleys 110 may be sharp or blunt. The peaks 108 may lie upon, or follow, the interior surface of the socket 100. The valleys 110 may be described as indentations into the interior surface of the socket 100, and thus the valleys 110 may also follow the interior surface of the socket 100, albeit offset below the interior surface. The valleys 110 may follow the interior surface exactly with a constant offset, or generally, with a variable offset. The internal corrugation 112 may be intact, or uninterrupted, throughout its extent so that all of the peaks 108 and valleys 110 are intact.

The internal corrugations 112 may be formed by a series of indentations, or valleys 110, which are patterned longitudinally within the socket 100. This arrangement is best seen in FIG. 14B. The longitudinal progression per valley 100 along the socket 100 may be constant or variable. FIG. 14B includes a sketch of the geometry used to define the internal corrugations 112, which illustrates a variable longitudinal progression.

In use, the head 20 may be inserted into the socket 100 with the axes 36, 102 aligned or coaxial (FIG. 11B, left), or misaligned (FIG. 11B, right), as described above for socket 40. In either arrangement, the external corrugations 30 of the head 20 may engage with the internal corrugation feature 112 of the socket 100 to lock the head 20 at a range of angles with respect to the socket 100. The incongruent shapes of the head 20 and socket 100 provide alternating zones of contact and clearance between the head 20 and the socket 100. Contact occurs between the sides 104 and the head 20, and clearance occurs between the corners 106 and the head 20.

Socket 100 may provide a more uniform polyaxial connection with the head 20 than that provided by the previous sockets 40, 70. Socket 100 is shown with five sides 104, while socket 40 is shown with four sides 42, and socket 70 is shown with six sides 74. Sockets with an even number of sides have facing sides and facing corners. The internal width of the socket is less between facing sides than it is between facing corners. The resistance to head engagement in the socket when the head is angled toward a corner is less than the resistance when the head is angled toward a side. In contrast, the socket 100 has an odd number of sides. Each side 104 faces a corner 106. The resistance to head engagement may be less directional for socket 100 than for sockets 40 or 70.

FIGS. 15A-B show yet another socket 120 for use with the head 20 in a polyaxial locking interconnection. Socket 120 illustrates a principle that applies to any of the sockets disclosed herein. The sockets 40, 70, and 100 are all shown extending perpendicular to, or normal to, a device surface surrounding the socket. It will be appreciated that this is a design convenience. Any of the sockets disclosed herein may extend into a device at an acute angle which, in this specification, is defined as an angle which is greater than zero degrees and less than ninety degrees. FIG. 15A-B show that socket 120 extends into a device at an acute angle 114. Otherwise, socket 120 is the same as socket 100, and may provide the same advantages with regard to uniform head 20 insertion effort at various head insertion angles.

FIGS. 17A-17C show yet another socket 130 for use with head 20. Socket 130 is another noncircular hole, which may have a longitudinal axis 132. The socket 130 may be formed in any medical device component, such as a plate, washer, rod, link, bone-contacting component, articular component, and the like. The socket 130 may extend completely through a component, or only partially through the component. The socket 130 may include two or more sides in a polygonal or poly-lobular arrangement. The socket 130 may have five sides 134 and five rounded corners 136, however the corners 136 may be sharp instead. The sides 134 may bulge toward the interior of the socket 130. The socket 130 may have a constant cross-sectional geometry over the full depth of the socket 130. Alternatively, the socket 130 may taper (FIG. 17B) or bulge along its length. The socket 130 may have a spherical or partial spherical interior. The socket 130 may twist along its depth.

The socket 130 includes an internal corrugation 138 which includes alternating peaks 140 and valleys 142 along the depth of the socket 130 or a portion thereof. The peaks 140 and/or valleys 142 may be sharp or blunt. The peaks 140 may lie upon, or follow, the interior surface of the socket 130. The valleys 142 may be described as indentations into the interior surface of the socket 130, and thus the valleys 142 may also follow the interior surface of the socket 130, albeit offset below the interior surface. The valleys 142 may follow the interior surface exactly with a constant offset, or generally, with a variable offset. The internal corrugation 138 may be intact, or uninterrupted, throughout its extent so that all of the peaks 140 and valleys 142 are intact.

The internal corrugations 138 may be formed by a single indentation, or valley 142, which winds around the socket 130 while progressing longitudinally within the socket 130. This arrangement is best seen in FIG. 17B. More than one indentation may be present. Additional indentations may wind around the socket 130 with the single indentation. The longitudinal progression per circuit around the socket 130 may be constant or variable. FIG. 17C shows a sketch depicting a sweep profile 144 for the corrugation 138. Sockets 40, 70 may each employ a similar sweep profile for the corrugations 46, 78. Where more than one indentation is present, a similar number of sweep profiles may be included.

In use, the head 20 may be inserted into the socket 130 with the axes 36, 132 aligned or coaxial, or misaligned, as described above for socket 40. In either arrangement, the external corrugations 30 of the head 20 may engage with the internal corrugation feature 138 of the socket 130 to lock the head 20 at a range of angles with respect to the socket 130. The incongruent shapes of the head 20 and socket 130 provide alternating zones of contact and clearance between the head 20 and the socket 130. Contact occurs between the sides 134 and the head 20, and clearance occurs between the corners 136 and the head 20. Socket 130 may provide the same advantages with regard to uniform head 20 insertion effort at various head insertion angles as does socket 100.

FIGS. 18A-18B show yet another socket 150 for use with the head 20 in a polyaxial locking interconnection. Socket 150 is another noncircular hole, which may have a longitudinal axis 152. The socket 150 may be formed in any medical device component, such as a plate, washer, rod, link, bone-contacting component, articular component, and the like. The socket 150 may extend completely through a component, or only partially through the component. The socket 150 may include two or more sides in a polygonal or poly-lobular arrangement. The socket 150 may have six sides 154 and six rounded corners 156, however the corners 156 may be sharp instead. The sides 154 may bulge toward the interior of the socket 150. The socket 150 may have a constant cross-sectional geometry over the full depth of the socket 150. Alternatively, the socket 150 may taper (FIG. 18A) or bulge along its length. The socket 150 may have a spherical or partial spherical interior. The socket 150 may twist along its depth.

The socket 150 includes an internal corrugation 158 which includes alternating peaks 160 and valleys 162 along the depth of the socket 150 or a portion thereof. The peaks 160 and/or valleys 162 may be sharp or blunt. The peaks 160 may lie upon, or follow, the interior surface of the socket 150. The valleys 162 may be described as indentations into the interior surface of the socket 150, and thus the valleys 162 may also follow the interior surface of the socket 150, albeit offset below the interior surface. The valleys 162 may follow the interior surface exactly with a constant offset, or generally, with a variable offset. The internal corrugation 158 may be intact, or uninterrupted, throughout its extent so that all of the peaks 160 and valleys 162 are intact.

The internal corrugations 158 may be formed by a single indentation, or valley 162, which winds around the socket 150 while progressing longitudinally within the socket 150. This arrangement is best seen in FIG. 18B. More than one indentation may be present. Additional indentations may wind around the socket 150 with the single indentation. The longitudinal progression per circuit around the socket 150 may be constant or variable.

In use, the head 20 may be inserted into the socket 150 with the axes 36, 152 aligned or coaxial, or misaligned, as described above for socket 40. In either arrangement, the external corrugations 30 of the head 20 may engage with the internal corrugation feature 158 of the socket 150 to lock the head 20 at a range of angles with respect to the socket 150. The incongruent shapes of the head 20 and socket 150 provide alternating zones of contact and clearance between the head 20 and the socket 150. Contact occurs between the sides 154 and the head 20, and clearance occurs between the corners 156 and the head 20. Socket 150 may provide the same advantages with regard to uniform head 20 insertion effort at various head insertion angles as does socket 100.

While the present disclosure has been made with reference to regularly shaped sockets 40, 70, 100, 120, 130, 150, these sockets may also be irregularly formed so that the spacing and size of each feature in a socket may be different. For example, each corner may have a unique radius. This applies to each feature described and shown herein. Any of the sockets disclosed herein may transform over its length from a first polygon shape to a second shape. The second shape may be a different polygon shape, a circle, or another profile.

FIGS. 19A-28E show additional socket embodiments.

Referring to FIGS. 19A-19E, another socket 170 is configured for use with the head 20 in a polyaxial locking interconnection. Socket 170 is another noncircular hole, which may have a longitudinal axis 172. The socket 170 may be formed in any medical device component, such as a plate, washer, rod, link, bone-contacting component, articular component, and the like. The socket 170 may extend completely through a component, or only partially through the component. The socket 170 may include two or more sides in a polygonal or poly-lobular arrangement. The socket 170 may have five sides 174 evenly interspersed with five rounded corners 176, however the corners 176 may be sharp instead. The sides 174 may bulge toward the interior of the socket 170. In the example shown in FIG. 19B, the sides 174 are of equal width relative to one another at any given transverse cross-section; in other embodiments the individual sides may differ in length from one another. The socket 170 may have a constant cross-sectional geometry over the full length of the socket 170. Alternatively, the socket 170 may taper, having a greater diameter at one end than at the opposite end of the socket (FIGS. 19B, 19E) or bulge along its length. The socket 170 may have a spherical or partial spherical interior. The socket 170 may twist along its length.

The socket 170 includes an internal corrugation 178 which includes alternating peaks 180 and valleys 182 along the length of the socket 170 or a portion thereof. The peaks 180 and/or valleys 182 may be sharp or blunt. The peaks 180 may lie upon, or follow, the interior surface of the socket 170. The valleys 182 may be described as indentations into the interior surface of the socket 170, and thus the valleys 182 may also follow the interior surface of the socket 170, albeit offset below the interior surface. The valleys 182 may follow the interior surface exactly with a constant offset, or generally, with a variable offset. The internal corrugation 178 may be intact, or uninterrupted, throughout its extent so that all of the peaks 180 and valleys 182 are intact.

The internal corrugations 178 may be formed by a single indentation, or valley 182, which winds around the socket 170 while progressing longitudinally within the socket 170. This arrangement is best seen in FIGS. 19D and 19E. More than one indentation may be present. Additional indentations may wind around the socket 170 with the single indentation. The longitudinal progression per circuit around the socket 170 may be constant or variable. The sides 174 may be of approximately equal width to one another in any one revolution of the valley 182.

Socket 170 includes a first end 184 which may be a top end, and a second end 186 which may be a bottom end. The internal corrugations 178 extend between the first end 184 and the second end 186. A counterbore 188 is formed adjacent to and in communication with socket 170. The counterbore 188 is immediately adjacent to the first end 184 of the socket 170, has an end surface 187, and is circumscribed by a sidewall 189. The end surface 187 may be orthogonal, or at a right angle, to the longitudinal axis 172. In the embodiment of FIGS. 19A-19E, the counterbore is a tapered polygonal pentagonal shape, similar to socket 170. The counterbore may be other shapes such as an oval, triangle, rectangle, pentagon, hexagon, heptagon, octagon, and so on. The counterbore may be symmetrical or asymmetrical, and may be the same shape or a different shape than the socket. As seen in FIGS. 19D and 19E, the counterbore 188 has a depth d parallel to longitudinal axis 172, and in the embodiment shown depth d is less than the length of socket 170; in other examples depth d may be equal or greater than the length of the socket. The degree of taper of the counterbore 188 may be greater than, equal to, or less than the degree of taper of the socket 170. The socket 170 may be centered relative to the counterbore 188 as seen in FIG. 19B; however in other examples the socket 170 may be offset relative to the counterbore. In the embodiment of FIGS. 19A-19E, the sidewall 189 of the counterbore 188 is straight in a longitudinal cross-section.

Referring to FIGS. 20A-20E, another socket 200 is configured for use with the head 20 in a polyaxial locking interconnection. Socket 200 has a longitudinal axis 202, and includes a noncircular socket portion 201 and a circular socket portion 203. In the example shown, the noncircular socket portion 201 is a top portion and the circular socket portion 203 is a bottom portion; in other examples their positions may be reversed. The socket 200 may be formed in any medical device component, such as a plate, washer, rod, link, bone-contacting component, articular component, and the like. The socket 200 may extend completely through a component, or only partially through the component. The noncircular portion 201 may include two or more sides in a polygonal or poly-lobular arrangement, forming a polygonal shape. The noncircular portion 201 may have five sides 204 and five rounded corners 206, however the corners 206 may be sharp instead. The sides 204 may bulge toward the interior of the socket 200. In the example shown in FIG. 20B, the sides 204 are of equal width relative to one another at any given transverse cross-section though the noncircular portion 201; in other embodiments the individual sides may differ in length from one another. The circle defined by the circular portion may be tangent to the sides 204, as can be seen in FIG. 20B. The socket 200 may have a constant cross-sectional geometry over the full length of the socket 200. Alternatively, the socket 200 may taper (FIGS. 20B, 20E) or bulge along its length. The socket 200 may have a spherical or partial spherical interior. The socket 200 may twist along its length.

The circular socket portion 203 can function as a safety feature, as it may restrict the ability to accidentally drive a fastener such as fastener 24 entirely through the medical device component containing the socket 200, by further retaining the head 20. The circular socket portion 203 may be shaped as a ledge protruding inwardly relative to the remainder of the socket 200. The transition between the noncircular socket portion 201 and the circular socket portion 203 may be smooth and continuous, or abrupt.

The socket 200 includes an internal corrugation 208 which includes alternating peaks 210 and valleys 212 along the noncircular socket portion thereof. The peaks 210 and/or valleys 212 may be sharp or blunt. The peaks 210 may lie upon, or follow, the interior surface of the socket 200. The valleys 212 may be described as indentations into the interior surface of the socket 200, and thus the valleys 212 may also follow the interior surface of the socket 200, albeit offset below the interior surface. The valleys 212 may follow the interior surface exactly with a constant offset, or generally, with a variable offset. The internal corrugation 208 may be intact, or uninterrupted, throughout its extent so that all of the peaks 210 and valleys 212 are intact. Throughout the circular socket portion 203, the internal corrugation 208 may be circular or helical.

The internal corrugation 208 may be formed by a single indentation, or valley 212, which winds around the socket 200 while progressing longitudinally within the socket 200. This arrangement is best seen in FIGS. 20D and 20E. More than one indentation may be present. Additional indentations may wind around the socket 200 with the single indentation. The longitudinal progression per circuit around the socket 200 may be constant or variable.

Socket 200 includes a first end 214 which may be a top end, and a second end 216 which may be a bottom end. The internal corrugation 208 extends between the first end 214 and the second end 216. A counterbore 218 is formed adjacent to and in communication with noncircular portion 201 of socket 200. The counterbore 218 is immediately adjacent to the first end 214 of the socket 200, has an end surface 217, and is circumscribed by a sidewall 219. The end surface 217 may be orthogonal, or at a right angle, to the longitudinal axis 202. In the embodiment of FIGS. 20A-20E, the counterbore is a tapered polygonal pentagonal shape, similar to noncircular socket portion 201. The counterbore may be other shapes such as circular, oval, triangle, rectangle, pentagon, hexagon, heptagon, octagon, and so on. The counterbore may be symmetrical or asymmetrical, and may be the same shape or a different shape than the socket. As seen in FIGS. 20D and 20E, the counterbore 218 has a depth d parallel to longitudinal axis 202, and in the embodiment shown depth d is less than the length of socket 200; in other examples depth d may be equal or greater than the length of the socket. The degree of taper of the counterbore 218 may be greater than, equal to, or less than the degree of taper of the socket 200. The socket 200 may be centered relative to the counterbore 218 as seen in FIG. 20B; however in other examples the socket 200 may be offset relative to the counterbore. In the embodiment of FIGS. 20A-20E, the sidewall 219 of the counterbore 218 is straight in a longitudinal cross-section.

Referring to FIGS. 21A-21E, another socket 220 is configured for use with the head 20 in a polyaxial locking interconnection. Socket 220 has a longitudinal axis 222, and includes a noncircular socket portion 221 and a circular socket portion 223. In the example shown, the noncircular socket portion 221 is a top portion and the circular socket portion 223 is a bottom portion; in other examples their positions may be reversed. The socket 220 may be formed in any medical device component, such as a plate, washer, rod, link, bone-contacting component, articular component, and the like. The socket 220 may extend completely through a component, or only partially through the component. The noncircular portion 221 may include two or more sides in a polygonal or poly-lobular arrangement. The noncircular portion 221 may have five sides 224 and five rounded corners 226, however the corners 226 may be sharp instead. The sides 224 may bulge toward the interior of the socket 220. In the example shown in FIG. 21B, the sides 224 are of equal length relative to one another at any given transverse cross-section through the noncircular portion 221; in other embodiments the individual sides may differ in length from one another. The circle defined by the circular portion 223 may be tangent to the sides 224 at the transition between the noncircular portion 221 and the circular portion 223, as can be seen in FIG. 21B. The socket 220 may taper (FIGS. 21B, 21E) or bulge along its length. The socket 220 may have a spherical or partial spherical interior. The socket 220 may twist along its length.

The circular socket portion 223 can function as a safety feature, as it may restrict the ability to accidentally drive a fastener such as fastener 24 entirely through the medical device component containing the socket 220, by further retaining the head 20. The circular socket portion 223 may be shaped as a ledge protruding inwardly relative to the remainder of the socket 220. The transition between the noncircular socket portion 221 and the circular socket portion 223 may be smooth and continuous, or abrupt.

The socket 220 includes an internal corrugation 228 which includes alternating peaks 230 and valleys 232 along the noncircular socket portion thereof. The peaks 230 and/or valleys 232 may be sharp or blunt. The peaks 230 may lie upon, or follow, the interior surface of the socket 220. The valleys 232 may be described as indentations into the interior surface of the socket 220, and thus the valleys 232 may also follow the interior surface of the socket 220, albeit offset below the interior surface. The valleys 232 may follow the interior surface exactly with a constant offset, or generally, with a variable offset. The internal corrugation 228 may be intact, or uninterrupted, throughout its extent so that all of the peaks 230 and valleys 232 are intact. Throughout the circular socket portion 223, the internal corrugation 228 may be circular or helical.

The internal corrugation 228 may be formed by a single indentation, or valley 232, which winds around the socket 220 while progressing longitudinally within the socket 220. This arrangement is best seen in FIGS. 21D and 21E. More than one indentation may be present. Additional indentations may wind around the socket 220 with the single indentation. The longitudinal progression per circuit around the socket 220 may be constant or variable.

Socket 220 includes a first end 234 which may be a top end, and a second end 236 which may be a bottom end. The internal corrugation 228 extends between the first end 234 and the second end 236. A counterbore 238 is formed adjacent to and in communication with noncircular portion 221 of socket 220. The counterbore 238 is immediately adjacent to the first end 234 of the socket 220, has an end surface 237, and is circumscribed by a sidewall 239. The end surface 237 may be orthogonal, or at a right angle, to the longitudinal axis 222. In the embodiment of FIGS. 21A-21E, the counterbore is a circular shape. The counterbore may be other shapes such as an oval, triangle, rectangle, pentagon, hexagon, heptagon, octagon, and so on. The counterbore may be symmetrical or asymmetrical, and may be the same shape or a different shape than the socket. As seen in FIGS. 21D and 21E, the counterbore 238 has a depth d parallel to longitudinal axis 222, and in the embodiment shown depth d is less than the length of socket 220; in other examples depth d may be equal or greater than the length of the socket. The degree of taper of the counterbore 238 may be greater than, equal to, or less than any degree of taper of the socket 220. The socket 220 may be centered relative to the counterbore 238 as seen in FIG. 21B; however in other examples the socket 220 may be offset relative to the counterbore. In the embodiment of FIGS. 21A-21E, the sidewall 239 of the counterbore 238 is straight in a longitudinal cross-section.

Referring to FIGS. 22A-22E, another socket 240 is configured for use with the head 20 in a polyaxial locking interconnection. Socket 240 has a longitudinal axis 242, and includes a noncircular socket portion 241 and a circular socket portion 243. In the example shown, the noncircular socket portion 241 is a first, or top portion and the circular socket portion 243 is a second, or bottom portion; in other examples their positions may be reversed. The socket 240 may be formed in any medical device component, such as a plate, washer, rod, link, bone-contacting component, articular component, and the like. The socket 240 may extend completely through a component, or only partially through the component. The noncircular portion 241 may include two or more sides in a polygonal or poly-lobular arrangement. The noncircular portion 241 may have five sides 244 and five rounded corners 246, however the corners 246 may be sharp instead. The sides 244 may bulge toward the interior of the socket 240. In the example shown in FIG. 22B, the sides 244 are of equal width relative to one another at any given transverse cross-section through the noncircular portion 241; in other embodiments the individual sides may differ in length from one another. The circle defined by the circular portion 243 may be tangent to the sides 244 at the transition between the noncircular portion 241 and the circular portion 243, as can be seen in FIG. 22B. The socket 240 may taper (FIGS. 22B, 22E) or bulge along its length. The socket 240 may have a spherical or partial spherical interior. The socket 240 may twist along its length.

The circular socket portion 243 can function as a safety feature, as it may restrict the ability to accidentally drive a fastener such as fastener 24 entirely through the medical device component containing the socket 240, by further retaining the head 20. The circular socket portion 243 may be shaped as a ledge protruding inwardly relative to the remainder of the socket 240. The transition between the noncircular socket portion 241 and the circular socket portion 243 may be smooth and continuous, or abrupt.

The socket 240 includes an internal corrugation 248 which includes alternating peaks 250 and valleys 252 along the noncircular socket portion thereof. The peaks 250 and/or valleys 252 may be sharp or blunt. The peaks 250 may lie upon, or follow, the interior surface of the socket 240. The valleys 252 may be described as indentations into the interior surface of the socket 240, and thus the valleys 252 may also follow the interior surface of the socket 240, albeit offset below the interior surface. The valleys 252 may follow the interior surface exactly with a constant offset, or generally, with a variable offset. The internal corrugation 248 may be intact, or uninterrupted, throughout its extent so that all of the peaks 250 and valleys 252 are intact. Throughout the circular socket portion 243, the internal corrugation 248 may be circular or helical.

The internal corrugation 248 may be formed by a single indentation, or valley 252, which winds around the socket 240 while progressing longitudinally within the socket 240. This arrangement is best seen in FIGS. 22D and 22E. More than one indentation may be present. Additional indentations may wind around the socket 240 with the single indentation. The longitudinal progression per circuit around the socket 240 may be constant or variable.

Socket 240 includes a first end 254 which may be a top end, and a second end 256 which may be a bottom end. The internal corrugation 248 extends between the first end 254 and the second end 256. A counterbore 258 is formed adjacent to and in communication with noncircular portion 241 of socket 240. The counterbore 258 is immediately adjacent to the first end 254 of the socket 240, and is circumscribed by a sidewall 259. In the embodiment of FIGS. 22A-22E, the counterbore is a circular, spherical shape. The counterbore may be other shapes such as an oval, triangle, rectangle, pentagon, hexagon, heptagon, octagon, and so on. The counterbore may be symmetrical or asymmetrical, and may be the same shape or a different shape than the socket. As seen in FIGS. 22D and 22E, the counterbore 258 has a depth d parallel to longitudinal axis 242, and in the embodiment shown depth d is less than the length of socket 240; in other examples depth d may be equal or greater than the length of the socket. The degree of taper of the counterbore 258 may be greater than, equal to, or less than any degree of taper of the socket 240. The socket 240 may be centered relative to the counterbore 258 as seen in FIG. 22B; however in other examples the socket 240 may be offset relative to the counterbore. In the embodiment of FIGS. 22A-22E, the sidewall 259 of the counterbore 258 is an arc of a circle in a longitudinal cross-section.

Referring to FIGS. 23A-23E, another socket 260 is configured for use with the head 20 in a polyaxial locking interconnection. Socket 260 is another noncircular hole, which may have a longitudinal axis 262. The socket 260 may be formed in any medical device component, such as a plate, washer, rod, link, bone-contacting component, articular component, and the like. The socket 260 may extend completely through a component, or only partially through the component. The socket 260 may include two or more sides in a polygonal or poly-lobular arrangement. The socket 260 may have five sides 264 and five rounded corners 266, however the corners 266 may be sharp instead. The sides 264 may bulge toward the interior of the socket 260. In the example shown in FIG. 23B, the sides 264 are of equal width relative to one another at any given transverse cross-section; in other embodiments the individual sides may differ in length from one another. The socket 260 may have a constant cross-sectional geometry over the full length of the socket 260. Alternatively, the socket 260 may taper (FIGS. 23B, 23E) or bulge along its length. The socket 260 may have a spherical or partial spherical interior. The socket 260 may twist along its length.

The socket 260 includes an internal corrugation 268 which includes alternating peaks 270 and valleys 272 along the length of the socket 260 or a portion thereof. The peaks 270 and/or valleys 272 may be sharp or blunt. The peaks 270 may lie upon, or follow, the interior surface of the socket 260. The valleys 272 may be described as indentations into the interior surface of the socket 260, and thus the valleys 272 may also follow the interior surface of the socket 260, albeit offset below the interior surface. The valleys 272 may follow the interior surface exactly with a constant offset, or generally, with a variable offset. The internal corrugation 268 may be intact, or uninterrupted, throughout its extent so that all of the peaks 270 and valleys 272 are intact.

The internal corrugations 268 may be formed by a single indentation, or valley 272, which winds around the socket 260 while progressing longitudinally within the socket 260. This arrangement is best seen in FIGS. 23D and 23E. More than one indentation may be present. Additional indentations may wind around the socket 260 with the single indentation. The longitudinal progression per circuit around the socket 260 may be constant or variable.

Socket 260 includes a first end 274 which may be a top end, and a second end 276 which may be a bottom end. The internal corrugations 268 extend between the first end 274 and the second end 276. A first counterbore 278 is formed adjacent to and in communication with socket 260. The first counterbore 278 is immediately adjacent to the first end 274 of the socket 260, has an end surface 277, and is circumscribed by a sidewall 279. The end surface 277 may be orthogonal, or at a right angle, to the longitudinal axis 262. In the embodiment of FIGS. 23A-23E, the first counterbore is a tapered polygonal pentagonal shape, similar to socket 260. The first counterbore may be other shapes such as an oval, triangle, rectangle, pentagon, hexagon, heptagon, octagon, and so on. The counterbore may be symmetrical or asymmetrical, and may be the same shape or a different shape than the socket. As seen in FIGS. 23D and 23E, the first counterbore 278 has a depth d parallel to longitudinal axis 262, and in the embodiment shown depth d is less than the length of socket 260; in other examples depth d may be equal or greater than the length of the socket. The degree of taper of the first counterbore 278 may be greater than, equal to, or less than the degree of taper of the socket 260. The socket 260 may be centered relative to the first counterbore 278 as seen in FIG. 23B; however in other examples the socket 260 may be offset relative to the counterbore. In the embodiment of FIGS. 23A-23E, the sidewall 279 of the first counterbore 278 is straight in a longitudinal cross-section.

A second counterbore 280 is formed adjacent to and in communication with socket 260. The second counterbore 280 is immediately adjacent to the second end 276 of the socket 260, has an end surface 283, and is circumscribed by a sidewall 281. The end surface 283 may be orthogonal, or at a right angle, to the longitudinal axis 262. In the embodiment of FIGS. 23A-23E, the second counterbore 280 is circular in shape, and is wider in diameter than the second end 276 of the socket 260. The second counterbore 280 may be equal in diameter to the first counterbore 278 where the first counterbore meets the first end 274. The second counterbore 280 is not tapered, and the sidewall 281 of the second counterbore 280 is straight in a longitudinal cross-section. However, other embodiments may include a second counterbore with a taper and/or an arced cross-section. Additional embodiments may include only one of the first or second counterbores. Of course, a first and/or second counterbore may be present adjacent to any of the sockets described herein.

Referring to FIGS. 24A-24E, another socket 290 is configured for use with the head 20 in a polyaxial locking interconnection. Socket 290 has a longitudinal axis 292, and the socket transitions from a noncircular shape to a circular shape along the axis 292. The socket 290 may be formed in any medical device component, such as a plate, washer, rod, link, bone-contacting component, articular component, and the like. The socket 290 may extend completely through a component, or only partially through the component. The socket 290 may include two or more sides in a polygonal or poly-lobular arrangement. The socket 290 may have five sides 294 and five rounded corners 296, however the corners 296 may be sharp instead. The sides 294 may bulge toward the interior of the socket 290. In the example shown in FIG. 24B, the sides 294 are of equal width relative to one another at any given transverse cross-section; in other embodiments the individual sides may differ in length from one another. The socket 290 may have a constant cross-sectional geometry over the full length of the socket 290. Alternatively, the socket 290 may taper (FIGS. 24B, 24E) or bulge along its length. The socket 290 may have a spherical or partial spherical interior. The socket 290 may twist along its length.

The socket 290 includes an internal corrugation 298 which includes alternating peaks 300 and valleys 302 along the length of the socket 290 or a portion thereof. The peaks 300 and/or valleys 302 may be sharp or blunt. The peaks 300 may lie upon, or follow, the interior surface of the socket 290. The valleys 302 may be described as indentations into the interior surface of the socket 290, and thus the valleys 302 may also follow the interior surface of the socket 290, albeit offset below the interior surface. The valleys 302 may follow the interior surface exactly with a constant offset, or generally, with a variable offset. The internal corrugation 298 may be intact, or uninterrupted, throughout its extent so that all of the peaks 300 and valleys 302 are intact.

The internal corrugations 298 may be formed by a single indentation, or valley 302, which winds around the socket 290 while progressing longitudinally within the socket 290. This arrangement is best seen in FIGS. 24D and 24E. More than one indentation may be present. Additional indentations may wind around the socket 290 with the single indentation. The longitudinal progression per circuit around the socket 290 may be constant or variable.

Socket 290 includes a first end 304 which may be a top end, and a second end 306 which may be a bottom end. The internal corrugations 298 extend between the first end 304 and the second end 306. At the first end 304, the socket assumes a pentagonal shape in a transverse cross sectional view or top down view (FIG. 24B) which transitions to a circular shape at the second end 306 (FIG. 24C). This transition may be described as a loft feature which may be a function of three-dimensional design software. The loft feature provides a gradual transition from one shape to the next along the longitudinal axis 292. It will be appreciated that socket 290 may also include a counterbore.

Referring to FIGS. 25A-25E, another socket 310 is configured for use with the head 20 in a polyaxial locking interconnection. Socket 310 has a longitudinal axis 312, and the socket transitions from a noncircular shape to a triangular shape along the axis 312; however any noncircular or polygonal shape is contemplated. The socket 310 may be formed in any medical device component, such as a plate, washer, rod, link, bone-contacting component, articular component, and the like. The socket 310 may extend completely through a component, or only partially through the component. The socket 310 may include two or more sides in a polygonal or poly-lobular arrangement. The socket 310 may have five sides 314 and five rounded corners 316, however the corners 316 may be sharp instead. The sides 314 may bulge toward the interior of the socket 310. In the example shown in FIG. 25B, the sides 314 are of equal width relative to one another; in other embodiments the individual sides may differ in length from one another. The socket 310 may have a constant cross-sectional geometry over the full length of the socket 310. Alternatively, the socket 310 may taper (FIGS. 25B, 25E) or bulge along its length. The socket 310 may have a spherical or partial spherical interior. The socket 310 may twist along its length.

The socket 310 includes an internal corrugation 318 which includes alternating peaks 320 and valleys 322 along the length of the socket 310 or a portion thereof. The peaks 320 and/or valleys 322 may be sharp or blunt. The peaks 320 may lie upon, or follow, the interior surface of the socket 310. The valleys 322 may be described as indentations into the interior surface of the socket 310, and thus the valleys 322 may also follow the interior surface of the socket 310, albeit offset below the interior surface. The valleys 322 may follow the interior surface exactly with a constant offset, or generally, with a variable offset. The internal corrugation 318 may be intact, or uninterrupted, throughout its extent so that all of the peaks 320 and valleys 322 are intact.

The internal corrugations 318 may be formed by a single indentation, or valley 322, which winds around the socket 310 while progressing longitudinally within the socket 310. This arrangement is best seen in FIGS. 25D and 25E. More than one indentation may be present. Additional indentations may wind around the socket 310 with the single indentation. The longitudinal progression per circuit around the socket 310 may be constant or variable.

Socket 310 includes a first end 324 which may be a top end, and a second end 326 which may be a bottom end. The internal corrugations 318 extend between the first end 324 and the second end 326. At the first end 324, the socket assumes a pentagonal shape in a transverse cross sectional view or top down view (FIG. 25B) which transitions to a triangular shape, or any noncircular or polygonal shape is contemplated, at the second end 326 (FIG. 25C). This transition may be described as a loft feature which may be a function of three-dimensional design software. The loft feature provides a gradual transition from one shape to the next along the longitudinal axis 312.

Referring to FIGS. 26A-26E, another socket 330 is configured for use with the head 20 in a polyaxial locking interconnection. Socket 330 has a longitudinal axis 332, and the socket twists along the longitudinal axis 332. The socket 330 may be formed in any medical device component, such as a plate, washer, rod, link, bone-contacting component, articular component, and the like. The socket 330 may extend completely through a component, or only partially through the component. The socket 330 may include two or more sides in a polygonal or poly-lobular arrangement. At any point along the longitudinal axis 332, the socket 330 may have five sides 334 and five rounded corners 336, however the corners 336 may be sharp instead. The sides 334 may bulge toward the interior of the socket 330. In the example shown in FIG. 26B, the sides 334 are of equal width relative to one another at any given transverse cross-section; in other embodiments the individual sides may differ in length from one another. The socket 330 may have a constant cross-sectional geometry over the full length of the socket 330. Alternatively, the socket 330 may taper (FIGS. 26B, 26E) or bulge along its length. The socket 330 may have a spherical or partial spherical interior. The socket 330 twists along its length.

The socket 330 includes an internal corrugation 338 which includes alternating peaks 340 and valleys 342 along the length of the socket 330 or a portion thereof. The peaks 340 and/or valleys 342 may be sharp or blunt. The peaks 340 may lie upon, or follow, the interior surface of the socket 330. The valleys 342 may be described as indentations into the interior surface of the socket 330, and thus the valleys 342 may also follow the interior surface of the socket 330, albeit offset below the interior surface. The valleys 342 may follow the interior surface exactly with a constant offset, or generally, with a variable offset. The internal corrugation 338 may be intact, or uninterrupted, throughout its extent so that all of the peaks 340 and valleys 342 are intact.

The internal corrugations 338 may be formed by a single indentation, or valley 342, which winds around the socket 330 while progressing longitudinally within the socket 330. This arrangement is best seen in FIGS. 26D and 26E. More than one indentation may be present. Additional indentations may wind around the socket 330 with the single indentation. The longitudinal progression per circuit around the socket 330 may be constant or variable.

Socket 330 includes a first end 344 which may be a top end, and a second end 346 which may be a bottom end. The internal corrugations 338 extend between the first end 344 and the second end 346. At the first end 344, the socket assumes a pentagonal shape in a transverse cross sectional view or top down view (FIG. 26B). Between the first and second ends 344, 346, the socket twists, remaining in a pentagonal shape throughout, and at the second end 346 (FIG. 26C). The twist of the socket 330 depicted in this embodiment is at an angle α of approximately 36° (FIG. 26B) from the first end 344 to the second 346 end, but there may be a greater or lesser degree of twist in other embodiments.

Referring to FIGS. 27A-27E, another socket 350 is configured for use with the head 20 in a polyaxial locking interconnection. Socket 350 is another noncircular hole, which may have a longitudinal axis 352. The socket 350 may be formed in any medical device component, such as a plate, washer, rod, link, bone-contacting component, articular component, and the like. The socket 350 may extend completely through a component, or only partially through the component. The socket 350 may include two or more sides in a polygonal or poly-lobular arrangement. The socket 350 may have five sides 354 and five rounded corners 356, however the corners 356 may be sharp instead. The sides 354 may bulge toward the interior of the socket 350. In the example shown in FIG. 27B, the sides 354 are of unequal width relative to one another at any given transverse cross-section to form an asymmetrical pentagonally shaped socket. In the example shown in FIGS. 27A-27E, one corner 356 is further displaced from the longitudinal axis 352 than the other corners. As a result, the two sides 354 immediately adjacent the displaced corner 356 are longer than the other sides 354. In other embodiments, more than one corner 356 may be further displaced from the longitudinal axis than the remaining corners. The socket 350 may have a constant cross-sectional geometry over the full length of the socket 350. Alternatively, the socket 350 may taper (FIGS. 27B, 27E) or bulge along its length. The socket 350 may have a spherical or partial spherical interior. The socket 350 may twist along its length.

The socket 350 includes an internal corrugation 358 which includes alternating peaks 360 and valleys 362 along the length of the socket 350 or a portion thereof. The peaks 360 and/or valleys 362 may be sharp or blunt. The peaks 360 may lie upon, or follow, the interior surface of the socket 350. The valleys 362 may be described as indentations into the interior surface of the socket 350, and thus the valleys 362 may also follow the interior surface of the socket 350, albeit offset below the interior surface. The valleys 362 may follow the interior surface exactly with a constant offset, or generally, with a variable offset. The internal corrugation 358 may be intact, or uninterrupted, throughout its extent so that all of the peaks 360 and valleys 362 are intact.

The internal corrugations 358 may be formed by a single indentation, or valley 362, which winds around the socket 350 while progressing longitudinally within the socket 350. This arrangement is best seen in FIGS. 27D and 27E. More than one indentation may be present. Additional indentations may wind around the socket 350 with the single indentation. The longitudinal progression per circuit around the socket 350 may be constant or variable.

Socket 350 includes a first end 364 which may be a top end, and a second end 366 which may be a bottom end. The internal corrugations 358 extend between the first end 364 and the second end 366. A counterbore 368 is formed adjacent to and in communication with socket 350. The counterbore 368 is immediately adjacent to the first end 364 of the socket 350, has an end surface 367, and is circumscribed by a sidewall 369. The end surface 367 may be orthogonal, or at a right angle, to the longitudinal axis 352. In the embodiment of FIGS. 27A-27E, the counterbore is a tapered polygonal pentagonal shape. In this example, the counterbore is a symmetrical pentagonal shape, unlike the asymmetrical socket 350. The counterbore may be other shapes such as an oval, triangle, rectangle, pentagon, hexagon, heptagon, octagon, and so on. The counterbore may be symmetrical or asymmetrical, and may be the same shape or a different shape than the socket. As seen in FIGS. 27D and 27E, the counterbore 368 has a depth d parallel to longitudinal axis 352, and in the embodiment shown depth d is less than the length of socket 350; in other examples depth d may be equal or greater than the length of the socket. The degree of taper of the counterbore 368 may be greater than, equal to, or less than the degree of taper of the socket 350. The socket 350 may be centered relative to the counterbore 368 as seen in FIG. 27B; however in other examples the socket 350 may be offset relative to the counterbore. In the embodiment of FIGS. 27A-27E, the sidewall 369 of the counterbore 368 is straight in a longitudinal cross-section.

Referring to FIGS. 28A-28E, another socket 370 is configured for use with the head 20 in a polyaxial locking interconnection. Socket 370 is another noncircular hole, which may have a longitudinal axis 372. The socket 370 may be formed in any medical device component, such as a plate, washer, rod, link, bone-contacting component, articular component, and the like. The socket 370 may extend completely through a component, or only partially through the component. The socket 370 may include two or more sides in a polygonal or poly-lobular arrangement. The socket 370 may have five sides 374 and five rounded corners 376, however the corners 376 may be sharp instead. The sides 374 may bulge toward the interior of the socket 370. A concavity 375 is formed in each of the sides 374. The presence of the concavity may provide additional zones of contact and clearance between the socket 370 and the head 20 along each side 374. In the example shown in FIG. 28B, the sides 374 are of equal width relative to one another at any given transverse cross-section; in other embodiments the individual sides may differ in length from one another. The socket 370 may have a constant cross-sectional geometry over the full length of the socket 370. Alternatively, the socket 370 may taper (FIGS. 28B, 28E) or bulge along its length. The socket 370 may have a spherical or partial spherical interior. The socket 370 may twist along its length.

The socket 370 includes an internal corrugation 378 which includes alternating peaks 380 and valleys 382 along the length of the socket 370 or a portion thereof. The peaks 380 and/or valleys 382 may be sharp or blunt. The peaks 380 may lie upon, or follow, the interior surface of the socket 370. The valleys 382 may be described as indentations into the interior surface of the socket 370, and thus the valleys 382 may also follow the interior surface of the socket 370, albeit offset below the interior surface. The valleys 382 may follow the interior surface exactly with a constant offset, or generally, with a variable offset. The internal corrugation 378 may be intact, or uninterrupted, throughout its extent so that all of the peaks 380 and valleys 382 are intact.

The internal corrugations 378 may be formed by a single indentation, or valley 382, which winds around the socket 370 while progressing longitudinally within the socket 370. This arrangement is best seen in FIGS. 28D and 28E. More than one indentation may be present. Additional indentations may wind around the socket 370 with the single indentation. The longitudinal progression per circuit around the socket 370 may be constant or variable. The sides 374 may be of approximately equal width to one another in any one revolution of the valley 382.

Socket 370 includes a first end 384 which may be a top end, and a second end 386 which may be a bottom end. The internal corrugations 378 extend between the first end 384 and the second end 386. A counterbore 388 is formed adjacent to and in communication with socket 370. The counterbore 388 is immediately adjacent to the first end 384 of the socket 370, has an end surface 387, and is circumscribed by a sidewall 389. The end surface 387 may be orthogonal, or at a right angle, to the longitudinal axis 372. In the embodiment of FIGS. 28A-28E, the counterbore is a tapered polygonal pentagonal shape, similar to socket 370. The counterbore may be other shapes such as an oval, triangle, rectangle, pentagon, hexagon, heptagon, octagon, and so on. The counterbore may be symmetrical or asymmetrical, and may be the same shape or a different shape than the socket. As seen in FIGS. 28D and 28E, the counterbore 388 has a depth d parallel to longitudinal axis 372, and in the embodiment shown depth d is less than the length of socket 370; in other examples depth d may be equal or greater than the length of the socket. The degree of taper of the counterbore 388 may be greater than, equal to, or less than the degree of taper of the socket 370. The socket 370 may be centered relative to the counterbore 388 as seen in FIG. 28B; however in other examples the socket 370 may be offset relative to the counterbore. In the embodiment of FIGS. 28A-28E, the sidewall 389 of the counterbore 388 is straight in a longitudinal cross-section.

Any of the socket embodiments recited herein may include a counterbore. Any of the counterbores described herein, for example but not limited to counterbores 188, 238, 258, and 280 may be positioned in the surface of a medical device component and provide a cleaner transition from the medical device component surface to the adjacent socket. Each counterbore may also provide a location for an instrument to seat or dock to the medical device component having the counterbore and socket. In particular, the non-spherical and/or polygonal counterbores, such as 188 and 388 for example, may prevent unwanted instrument rotation relative to the medical device component when the instrument is docked in the counterbore. Further, any of the counterbores may serve as a recess in the medical device component for a portion of a fastener such as head 20, thus providing a lower profile construction. The presence of a counterbore adjacent a socket can also allow for a fastener such as a screw to pass through the socket without locking to the socket, by retention of the head in the counterbore.

The components disclosed herein may be fabricated from metals, alloys, polymers, plastics, ceramics, glasses, composite materials, or combinations thereof, including but not limited to: PEEK, titanium, titanium alloys, commercially pure titanium grade 2, ASTM F67, Nitinol, cobalt chrome, stainless steel, ultra high molecular weight polyethylene (UHMWPE), biocompatible materials, and biodegradable materials, among others. Different materials may be used for different parts. Coatings may be present. Different materials may be used within a single part. Any component disclosed herein may be colored, coded or otherwise marked to make it easier for a user to identify the type and size of the component, the setting, the function(s) of the component, and the like.

It should be understood that the present systems, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several examples for the purpose of streamlining the disclosure. This method of disclosure is not to be interpreted as reflecting an intention that the examples of the invention require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

The invention claimed is:

1. A locking connection comprising:
a head comprising external corrugations; and
a noncircular socket, wherein the socket receives the head, wherein the socket comprises a depth, wherein the socket comprises internal corrugations.

2. The locking connection of claim 1, wherein the socket extends partially through a component.

3. The locking connection of claim 2, wherein the socket extends into the component at an acute angle.

4. The locking connection of claim 1, wherein the socket comprises multiple sides and corners.

5. The locking connection of claim 4, wherein the socket comprises an odd number of sides and corners.

6. The locking connection of claim 4, wherein the sides bulge toward an interior of the socket.

7. The locking connection of claim 1, wherein the socket tapers along the depth.

8. The locking connection of claim 1, wherein the socket twists along the depth.

9. The locking connection of claim 1, wherein the internal corrugations are uninterrupted throughout their extent.

10. The locking connection of claim 1, wherein the internal corrugations comprise alternating peaks and valleys along the depth, wherein the peaks and valleys follow an interior surface of the socket.

11. The locking connection of claim 10, wherein the peaks and valleys follow the interior surface with a constant offset.

12. The locking connection of claim 10, wherein the peaks and valleys follow the interior surface with a variable offset.

13. The locking connection of claim 10, wherein the internal corrugations comprise a series of peaks and valleys.

14. The locking connection of claim 13, wherein the peaks and valleys are patterned longitudinally within the socket.

15. The locking connection of claim 14, wherein a longitudinal progression per valley is constant.

16. The locking connection of claim 14, wherein a longitudinal progression per valley is variable.

17. The locking connection of claim 1, wherein the socket receives the head at any of a plurality of orientations of the head relative to the socket.

* * * * *